United States Patent [19]

Larson, Jr. et al.

[11] Patent Number: 5,722,429

[45] Date of Patent: Mar. 3, 1998

[54] CONNECTING ARRANGEMENT FOR MEDICAL DEVICE

[75] Inventors: Carl O. Larson, Jr., Stonington; James S. Smith, Old Lyme; John H. Chapman, Groton; Scot A. Slimon, Mystic; John D. Trahan, No. Stonington, all of Conn.; Robert J. Brozek, Bridgewater, N.J.; Alberto Franco, Hazlet, N.J.; John J. McGarvey; Marvin E. Rosen, both of Elizabeth, N.J.; Michael K. Pasque, St. Louis, Mo.

[73] Assignee: Electric Boat Corporation, Groton, Conn.

[21] Appl. No.: 477,909

[22] Filed: Jun. 7, 1995

Related U.S. Application Data

[60] Division of Ser. No. 201,806, Feb. 25, 1994, Pat. No. 5,676,651, which is a continuation-in-part of Ser. No. 35,788, Mar. 23, 1993, Pat. No. 5,290,227, which is a continuation-in-part of Ser. No. 926,779, Aug. 6, 1992, abandoned.

[51] Int. Cl.$^6$ ..................................................... A61B 19/00
[52] U.S. Cl. ........................... 128/899; 600/16; 623/3
[58] Field of Search ................................. 600/30, 36, 16, 600/17; 606/153, 158; 623/1, 2, 3, 900; 128/899

[56] References Cited

U.S. PATENT DOCUMENTS

| | | |
|---|---|---|
| 424,535 | 4/1890 | Bock. |
| 458,872 | 9/1891 | Van Depoele. |
| 1,684,468 | 9/1928 | Brown. |
| 1,822,242 | 9/1931 | Schongut. |
| 2,061,869 | 11/1936 | Gilbert et al.. |
| 2,515,110 | 7/1950 | Bornstein. |
| 2,690,128 | 9/1954 | Basilewsky. |
| 2,701,331 | 2/1955 | Holst. |
| 3,134,938 | 5/1964 | Morgan. |
| 3,172,027 | 3/1965 | Bourke et al.. |
| 3,233,607 | 2/1966 | Bolie. |
| 3,282,219 | 11/1966 | Blackwell et al.. |
| 3,287,616 | 11/1966 | McNeile. |
| 3,328,656 | 6/1967 | Dotson. |

(List continued on next page.)

FOREIGN PATENT DOCUMENTS

| | | |
|---|---|---|
| 0350302 | 11/1975 | European Pat. Off.. |
| 0203222 | 11/1985 | European Pat. Off.. |
| 0198617 | 3/1986 | European Pat. Off.. |
| 0237145 | 1/1987 | European Pat. Off.. |

(List continued on next page.)

OTHER PUBLICATIONS

English language abstract of FR 2 309 206.
Cathey, Jimmie J. et al., "A Tubular Self–Synchronous Motor for Artificial Heart Pump Drive", IEEE Transactions on Biomedical Engineering, Mar. 1996, vol. BME–33, No. 3, pp. 315–319.
English language abstract of Soviet Union patent No. 1,284,556, Jan. 23, 1987.

(List continued on next page.)

*Primary Examiner*—William E. Kamm
*Attorney, Agent, or Firm*—Brumbaugh, Graves, Donohue & Raymond

[57] ABSTRACT

In one embodiment described in the specification, a surgically implantable reciprocating pump employs a check valve as the piston, which is driven by a permanent magnet linear electric motor to assist either side of the natural heart. The pump is implanted in the aorta or pulmonary artery using vascular attachment cuffs such as flexible cuffs for suturing at each end with the pump output directly in line with the artery. The pump is powered by surgically implanted rechargeable batteries. In another embodiment, pairs of pumps are provided to replace or assist the natural heart or to provide temporary blood flow throughout the body, for example, during operations to correct problems with the natural heart.

8 Claims, 22 Drawing Sheets

U.S. PATENT DOCUMENTS

| | | |
|---|---|---|
| 3,443,128 | 5/1969 | Fakan . |
| 3,492,819 | 2/1970 | Waltrip . |
| 3,791,770 | 2/1974 | Farkos . |
| 3,836,289 | 9/1974 | Wolford et al. . |
| 3,842,440 | 10/1974 | Karlson . |
| 3,884,125 | 5/1975 | Massie . |
| 3,911,897 | 10/1975 | Leachman, Jr. . |
| 3,911,898 | 10/1975 | Leachman, Jr. . |
| 3,919,722 | 11/1975 | Harmison . |
| 4,005,346 | 1/1977 | Hsia . |
| 4,016,871 | 4/1977 | Schiff . |
| 4,101,816 | 7/1978 | Shepter . |
| 4,102,610 | 7/1978 | Taboada et al. . |
| 4,127,134 | 11/1978 | Ushakoff . |
| 4,210,409 | 7/1980 | Child . |
| 4,213,207 | 7/1980 | Wilson . |
| 4,220,899 | 9/1980 | von der Heide . |
| 4,221,548 | 9/1980 | Child . |
| 4,233,690 | 11/1980 | Akins . |
| 4,234,831 | 11/1980 | Kemmer et al. . |
| 4,262,414 | 4/1981 | Sugalski . |
| 4,272,226 | 6/1981 | Osborne . |
| 4,299,544 | 11/1981 | Masaka . |
| 4,332,541 | 6/1982 | Anders . |
| 4,344,022 | 8/1982 | von der Heide . |
| 4,370,577 | 1/1983 | Wakabayashi et al. . |
| 4,375,941 | 3/1983 | Child . |
| 4,389,169 | 6/1983 | De Dionigi . |
| 4,397,049 | 8/1983 | Robinson et al. . |
| 4,397,919 | 8/1983 | Ballard . |
| 4,434,389 | 2/1984 | Kollmorgen et al. . |
| 4,500,827 | 2/1985 | Merritt et al. . |
| 4,506,394 | 3/1985 | Bédard . |
| 4,516,567 | 5/1985 | Veragen . |
| 4,535,483 | 8/1985 | Klawitter et al. . |
| 4,541,787 | 9/1985 | DeLong . |
| 4,583,525 | 4/1986 | Suzuki et al. . |
| 4,610,658 | 9/1986 | Buchwald et al. . |
| 4,638,192 | 1/1987 | von der Heide . |
| 4,642,882 | 2/1987 | Castiglione et al. . |
| 4,650,486 | 3/1987 | Chareire . |
| 4,687,623 | 8/1987 | Cook . |
| 4,692,673 | 9/1987 | DeLong . |
| 4,705,516 | 11/1987 | Barone et al. . |
| 4,775,301 | 10/1988 | Cartwright et al. . |
| 4,790,843 | 12/1988 | Carpenter et al. . |
| 4,824,337 | 4/1989 | Lindner et al. . |
| 4,846,831 | 7/1989 | Skillin . |
| 4,868,431 | 9/1989 | Karita et al. . |
| 4,870,306 | 9/1989 | Petersen . |
| 4,892,541 | 1/1990 | Alonso . |
| 4,896,088 | 1/1990 | Jahns . |
| 4,897,563 | 1/1990 | Bahl . |
| 4,924,123 | 5/1990 | Hamajima et al. . |
| 4,935,030 | 6/1990 | Alonso . |
| 4,957,504 | 9/1990 | Chardack . |
| 4,965,864 | 10/1990 | Roth et al. . |
| 4,973,892 | 11/1990 | Murata et al. . |
| 4,979,955 | 12/1990 | Smith . |
| 5,035,709 | 7/1991 | Wieting et al. . |
| 5,064,353 | 11/1991 | Tsukahara . |
| 5,071,431 | 12/1991 | Sauter et al. . |
| 5,081,381 | 1/1992 | Narasaki . |
| 5,085,563 | 2/1992 | Collins et al. . |
| 5,089,014 | 2/1992 | Holfert . |
| 5,089,017 | 2/1992 | Young et al. . |
| 5,091,665 | 2/1992 | Kelly . |
| 5,123,919 | 6/1992 | Sauter et al. . |
| 5,136,194 | 8/1992 | Oudet et al. . |
| 5,146,123 | 9/1992 | Yarr . |
| 5,163,954 | 11/1992 | Curcio et al. . |
| 5,166,563 | 11/1992 | Bassine . |
| 5,178,633 | 1/1993 | Peters . |
| 5,179,306 | 1/1993 | Nasar . |
| 5,193,985 | 3/1993 | Escue et al. . |
| 5,207,707 | 5/1993 | Gourley . |
| 5,208,498 | 5/1993 | Hamajima . |
| 5,214,323 | 5/1993 | Ueda et al. . |
| 5,225,725 | 7/1993 | Shiraki et al. . |
| 5,236,451 | 8/1993 | Bokros et al. . |
| 5,242,995 | 9/1993 | Kim et al. . |
| 5,246,453 | 9/1993 | Bokros et al. . |
| 5,252,043 | 10/1993 | Bolding et al. . |
| 5,263,979 | 11/1993 | Isoyama et al. . |
| 5,360,445 | 11/1994 | Goldowsky . |

FOREIGN PATENT DOCUMENTS

| | | |
|---|---|---|
| 0310254 | 9/1988 | European Pat. Off. . |
| 2309206 | 11/1976 | France . |
| 2812481 | 3/1978 | Germany . |
| WO93-09348 | 5/1993 | WIPO . |

OTHER PUBLICATIONS

Article entitled: Engineering A Replacement For The Human Heart, Mechanical Engineering, Jul. 1991, pp. 36–43.

Daniel, Michael A., et al., "Clinical Evaluation of the Novacor Totally Implantable Ventricular Assist System", ASAIO Transactions 1991; 37:M423–M425.

Dörp, E., et al., "The measurement of blood density to investigate protein deposition at the blood/hollow fiber membrane interface during ultrafiltration", Int J Artif Organs 1991; 14:424–429.

Drasler, William J., et al., "A Unique Vascular Graft Concept for Coronary and Peripheral Applications", ASAIO Transactions 1988; 34:769–772.

Fischel, R.J., et al., "Couette Membrane Filtration with Constant Shear Stress", ASAIO Transactions 1988; 34:375–385.

Frazier, O.H., M.D., et al., "First Human Use of the Hemopump, a Catheter–Mounted Ventricular Assist Device", Ann Thorac Surg 1990; 49:299–304.

Haas, G., et al., "Effect of head–down bedrest on blood/plasma density after intravenous fluid load", Acta Physiol Scand 1992, 144, S604:113–120.

Hung, Ting–Cheng, et al., "Effects of Long–term Novacor Artificial Heart Support on Blood Rheology", ASAIO Transactions 1991; 37:M312–M313.

Hashimoto, Shigehiro, "Erythrocyte Destruction under Periodically Fluctuating Shear Rate: Comparative Study with Constant Shear Rate", Artif Organs 1989; 13(5):458–463.

Imachi, Kou, et al., "A New Pulsatile Total Artificial Heart Using a Single Centrifugal Pump", ASAIO Transactions 1991; 37:M242–M243.

Jurmann, Michael J., et al., "In Vivo Determinants of Energy Consumption in Electric Motor Driven Artificial Hearts", ASAIO Transactions 1989; 35:745–747.

Kenner, L, "The measurement of blood density and its meaning", Basic Res Cardiol 1989; 84:111–124.

Kim, Hee Chan, et al., "Development of An Automatic Control Algorithm for the Electrohydraulic Total Artificial Heart Without Transducers", ASAIO Transactions 1991; 37:M501–M503.

Kresh, J. Yasha, "Myocardial Mechanics and Energetics Revisited", Trans Am Soc Artif Intern Organs 1991; 37:537–539.

Lamson, Theodore C., et al., "Real–Time In Vitro Observation of Cavitation in a Prosthetic Heart Valve", ASAIO Transactions 1991; 37:M351–M353.

Lee, Jen–shih and Lee, Lian–pin, "A Density Method for Determining Plasma and Red Blood Cell Volume", Annals of Biomedical Engineering 1992; 20:195–204.

Lee, Sang H., et al., "Development of A Totally Implantable Total Artificial Heart Controller", ASAIO Transactions 1991; 37:M505–M507.

Levinson, Mark M., M.D., et al., "Indexes of Hemolysis in Human Recipients of the Jarvik-7 Total Artificial Heart: A Cooperative Report of Fifteen Patients", J. Heart Transplant 1986; 5:236–248.

Lioi, Anthony P., "In Vitro Development of Automatic Control for the Actively Filled Electrohydraulic Heart", Artif Organs 1988; 12(2)152–162.

McGee, Michael G. et al., "Extended Support with a Left Ventricular Assist Device as a Bridge to Heart Transplantation", ASAIO Transactions 1991; 37:M425–M426.

Miller, Douglas L., et al., "Mechanisms For Hemolysis By Ultrasonic Cavitation In The Rotating Exposure System", Ultrasound in Med & Biol 1991; 17(2):171–178.

Mitamura, Yoshinori, et al., "The Valvo–Pump: An Axial, Nonpulsatile Blood Pump", ASAIO Transactions 1991; 37:M510–M512.

Nakahara, Toro and Yoshida, Fumitake, "Mechanical effects on rates of hemolysis", Journal of Biomedical Materials Research 1986; 20:363–374.

Oaks, Timothy E., "Combined Registry for the Clinical Use of Mechanical Ventricular Assist Pumps and the Total Artificial Heart in Conjunction with Heart Transplantation: Fifth Official Report–1990", The Journal of Heart & Lung Transplantation 1991, vol. 10, No. 5, Part 1, pp. 621–625.

Perrone, B., "Evidence of Fluid Shifts during Dialysis Sessions with Sodium and Ultrafiltration Profiles", Contrib Nephrol. Basel, Karger 1989; 74:191–199.

Pierce, William S., M.D., et al., "An Electric Artificial Heart for Clinical Use", Ann Surg 1990, pp. 339–344.

Poirier, Victor L., "Can Our Society Afford Mechanical Hearts?", ASAIO Transactions 1991; 37:540–544.

Qian, Kun–xi, "Experience in Reducing the Hemolysis of an Impeller Assist Heart", ASAIO Transactions 1989; 35:46–53.

Qian, Kun–xi, "Haemodynamic approach to reducing thrombosis and haemolysis in an impeller pump", Biomechs 1990; 12:533–535.

Qian, K.X., et al., "The Realization of a Pulsatile Implantable Impeller Pump with Low Hemolysis", ASAIO Transactions 1989; 13:162–169.

Qian, K.X., et al., "Toward an Implantable Impeller Total Heart", ASAIO Transactions 1987; 33:704–707.

Sasaki, Tatsuya, et al., "A Biolized, Compact, Low Noise, High Performance Implantable Electrochemical Ventricular Assist System", ASAIO Transactions 1991; 37:M249–251.

Schneditz, D., et al., "Methods in clinical hemorheology: The continuous measurement of arterial blood density and blood sound speed in man", Biorheology 1990; 27:895–902.

Schneditz, D., "Sound Speed, Density and Total Protein Concentration of Blood", J. Clin. Chem. Clin. Biochem. 1989; 27:803–806.

Schoen, Frederick J., "Biomaterials Science, Medical Devices, and Artificial Organs", ASAIO Transactions 1991; 37:44–48.

Schoephoerster, Richard T. and Chandran, Krishnan B., "Velocity and Turbulence Measurements Past Mitral Valve Prostheses In A Model Left Ventricle", J. Biomechanics 1991; 24(7):549–562.

Shah, Aamir S., et al., "Intraoperative Determination of Mediastinal Constraints for a Total Artificial Heart", Trans Am Soc Artif Intern Organs 1991, vol. XXXVII, pp. 76–79.

Shiono, Motomi, et al., "Anatomic Fit Study for Development of a One Piece Total Artificial Heart", ASAIO Transactions 1991; 37:M254–M255.

Snyder, A., et al., "A Completely Implantable Total Artificial Heart System", ASAIO Transactions 1991; 37:M237–M238.

Taenaka, Yoshiyuki, et al., "Chronic Evaluation of a Compact Nonseal Magnet Pump as a Nonpulsatile Pump for Long–term Use", ASAIO Transactions 1991; 37:M243–M245.

Takatani, S., et al., "A Unique, Efficient, Implantable, Electromechanical, Total Artificial Heart", ASAIO Transactions 1991; 37:M238–M240.

Trinkl, J., et al., "Control of Pulsatile Rotary Pumps Without Pressure Sensors", ASAIO Transactions 1991; 37:M208–M210.

Tsach, Uri, et al., "Minimum Power Consumption of the Electric Ventricular Assist Device Through the Design of an Opitmal Output Controller", ASAIO Transactions 1987; 38:714–719.

Van Meurs, Krisa P., et al., "Maximum Blood Flow Rates for Arterial Cannulae Used in Neonatal ECMO", ASAIO Transactions 1990; 36:M679–M681.

Wampler, Richard K., et al., "In Vivo Evaluation of a Peripheral Vascular Access Axial Flow Blood Pump", Trans Am Soc Artif Intern Organs 1988, vol. XXXIV, pp. 450–454.

Weiss, William J., et al., "In Vivo Performance of a Transcutaneous Energy Transmission System with the Penn State Motor Driven Ventricular Assist Device", ASAIO Transactions 1989; 35:284–288.

Weiss, William J., et al., "Permanent Circulatory Support Systems at The Pennsylvania State University", IEE Transactions on Biomedical Engineering 1990, vol. 37, No. 2, pp. 138–145.

Wipf, Stefan L., "Spherical Rotary Piston Machine as an Artificial Heart", ASIAO Transactions 1991; 37:M246–M247.

Woodard, John C., et al., "A Sophisticated Electromechanical Ventricular Simulator for Ventricular Assist System Testing", ASAIO Transactions 1991; 37:M210–M211.

Yoganathan, Ajit P., Ph.D., et al., "In vitro velocity and turbulence measurements in the vicinity of three new mechanical aortic heart valve prostheses: Björk–Shiley Monostrut, Omni–Carbon, and Duromedics", J. Thoracic Cardiovasc Surg 1988; 95:929–939.

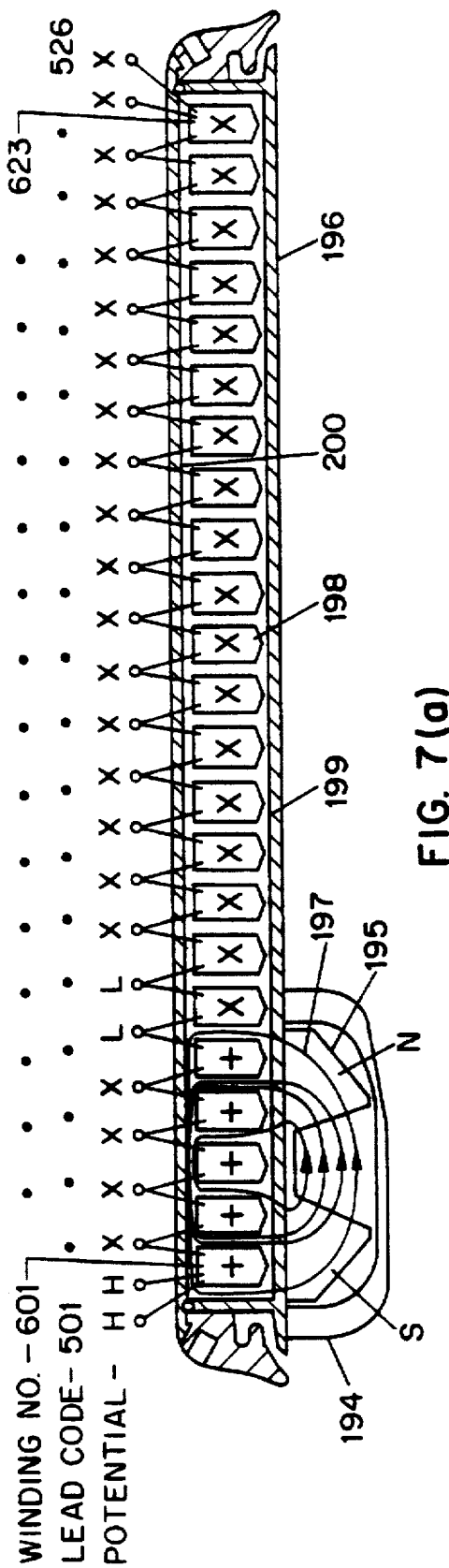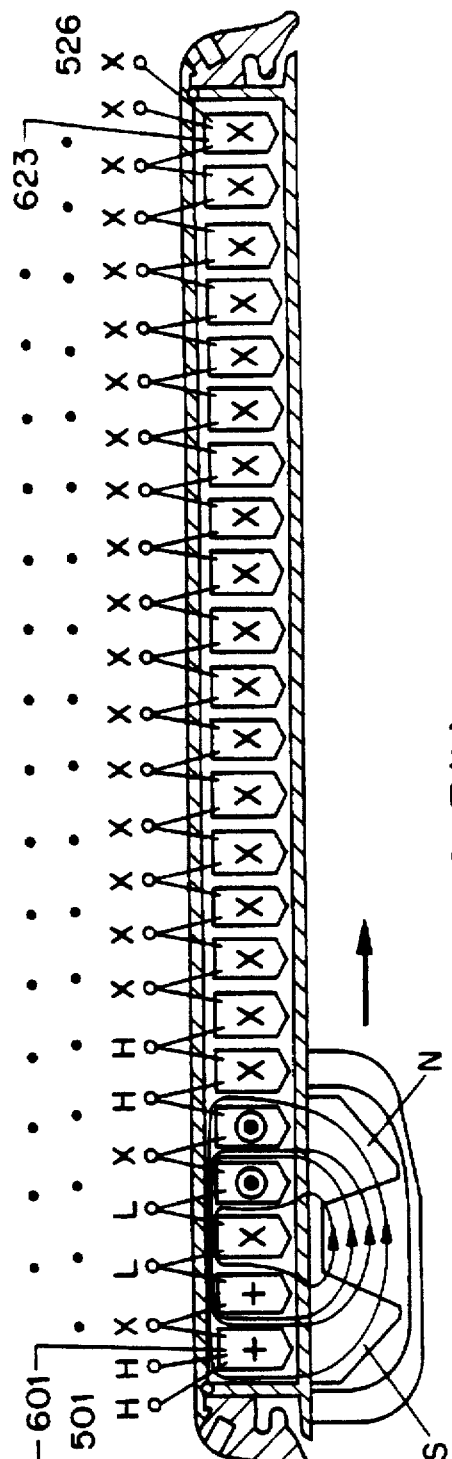

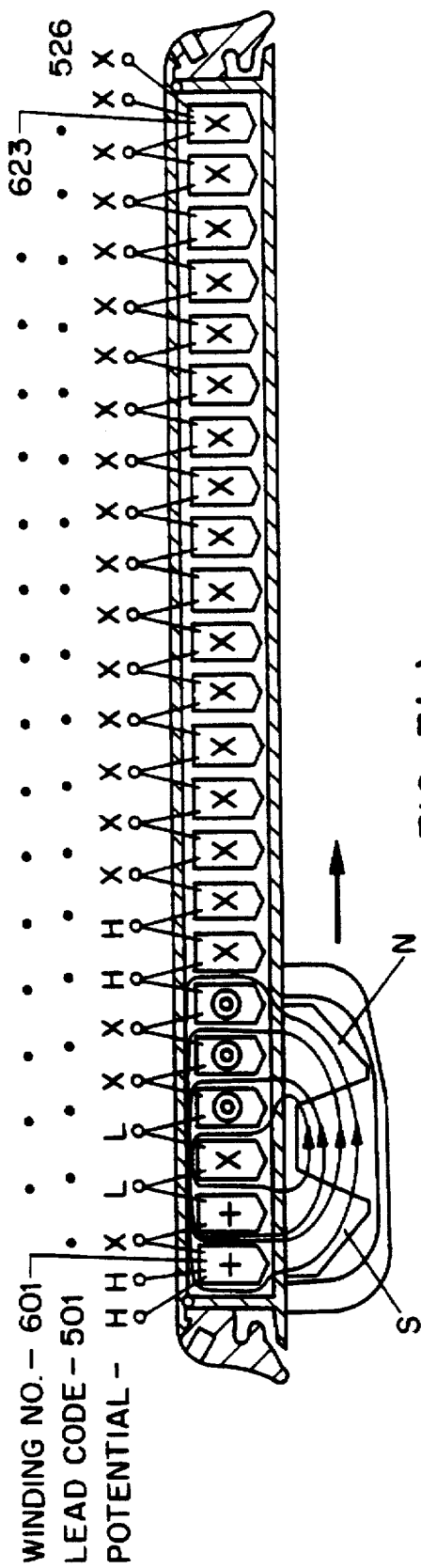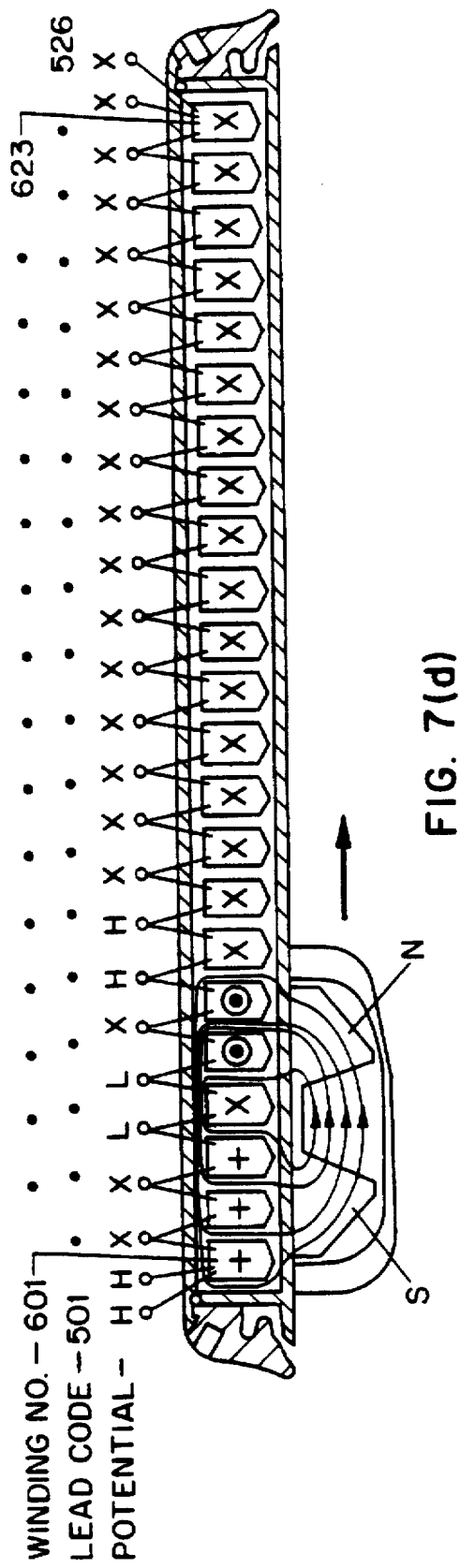

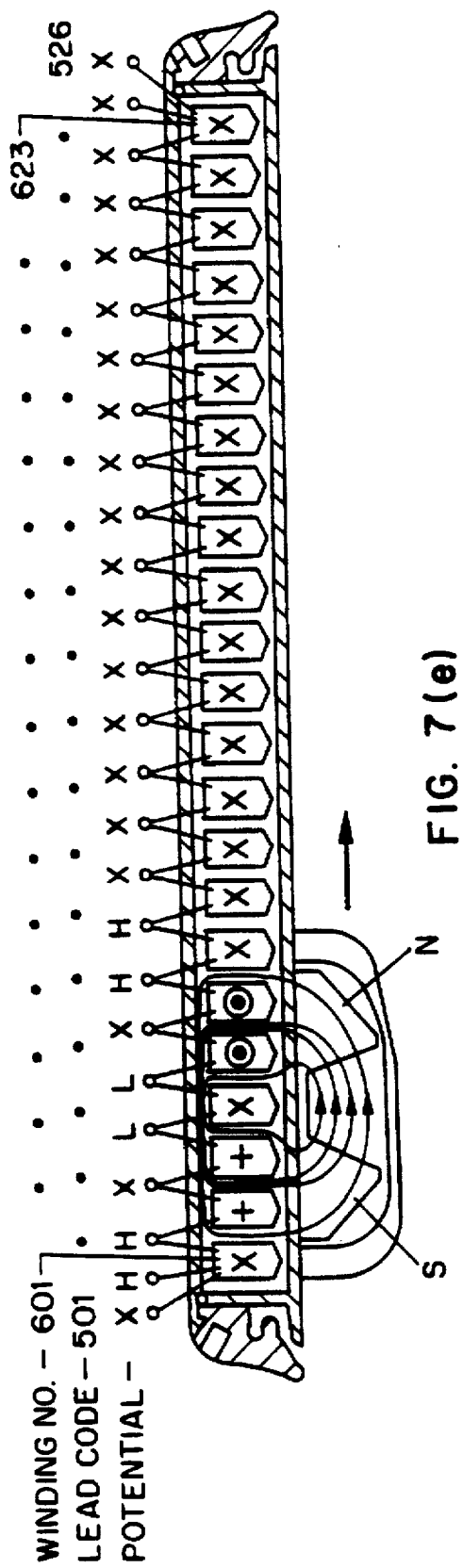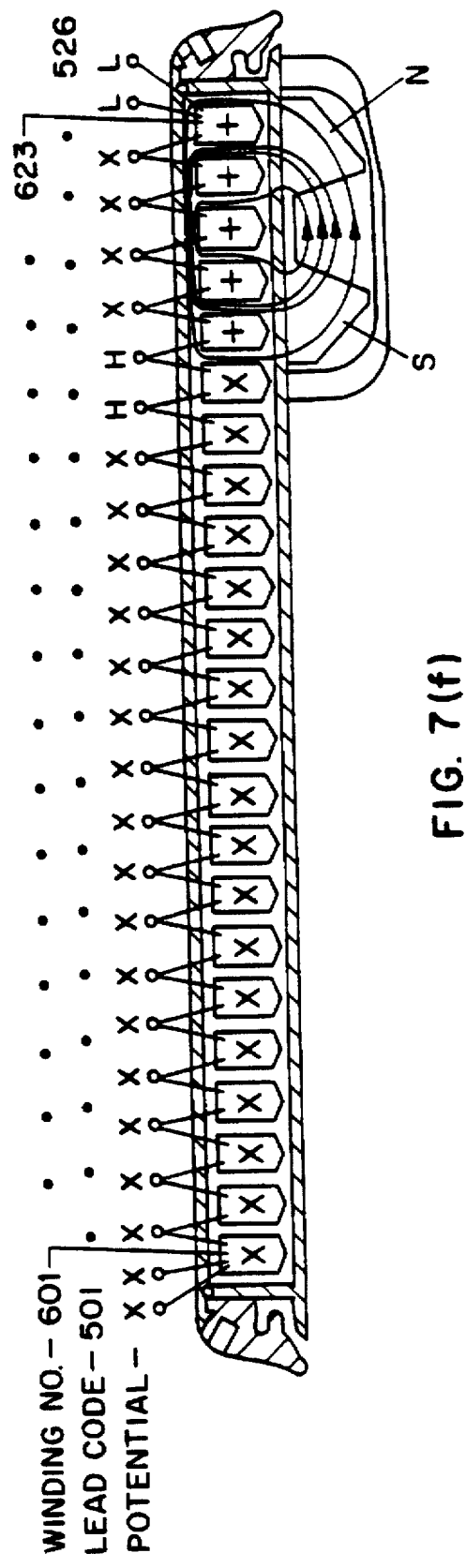

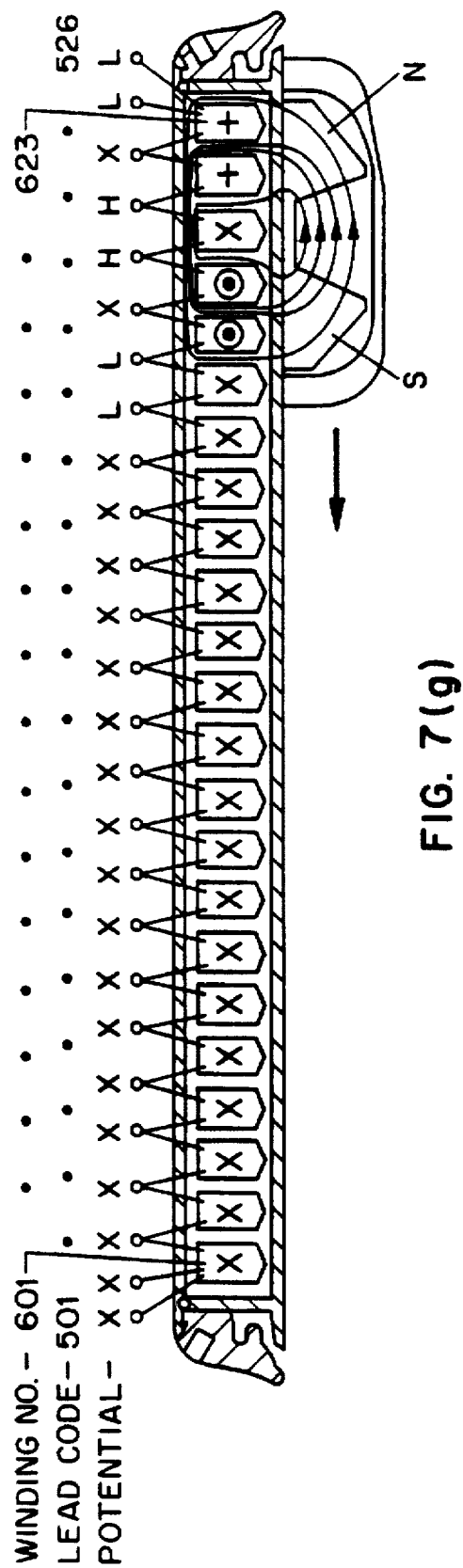
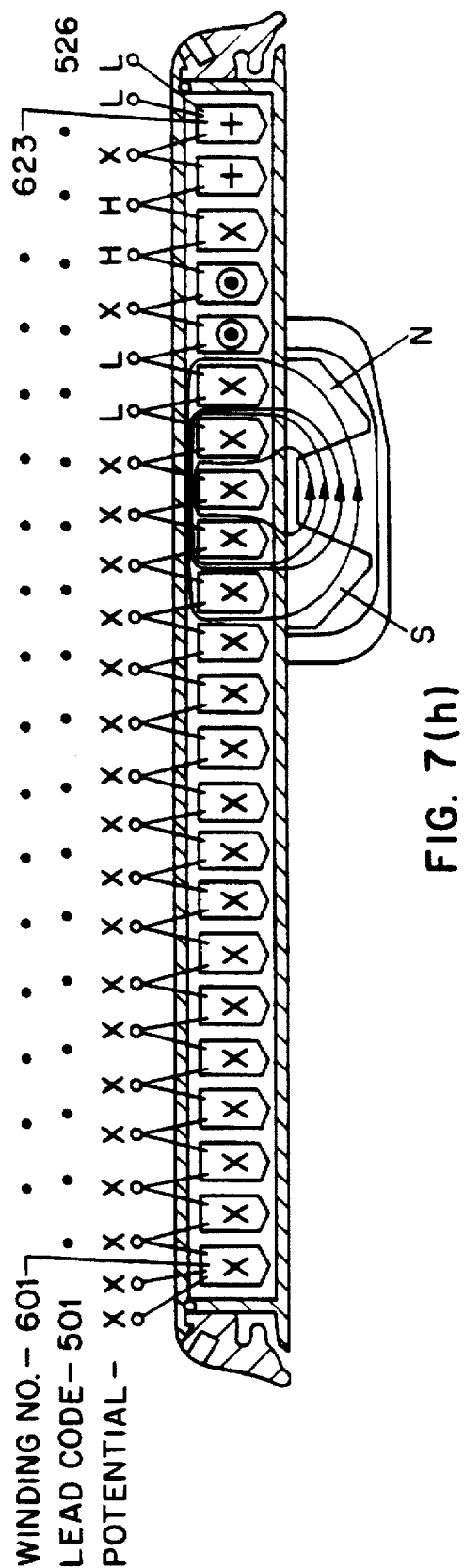
FIG. 7(g)
FIG. 7(h)

CONNECTING ARRANGEMENT FOR MEDICAL DEVICE

CROSS-REFERENCE TO RELATED APPLICATIONS

This application is a division of U.S. Ser. No. 08/201,806 filed on Feb. 25, 1994, now U.S. Pat. No. 5,676,651, which is a continuation-in-part of U.S. Ser. No. 08/035,788 filed Mar. 23, 1993, which issued as U.S. Pat. No. 5,290,227, which is a continuation-in-part of U.S. Ser. No. 07/926,779, filed Aug. 6, 1992, now abandoned.

BACKGROUND OF THE INVENTION

This invention relates to reciprocating pump arrangements for pumping fluids such as blood in a controlled manner. More specifically, this invention is directed to a reciprocating pump capable of providing optimal assistance for ventricular or cardiac support such as that for an ailing ventricle. It produces effective pumping action under minimum shear conditions.

Heretofore a number of pump designs have been proposed for pumping fluids such as blood. Such pumps must provide leak-free operation and must avoid contamination of the fluid by the pump components and the external environment. In addition, such pumps must effectively pump the fluid at a suitable rate without applying excessive Reynolds shear stress to the fluid. Damage due to excessive shear is particularly a problem when pumping fluids such as blood or blood products.

It is well known to those skilled in the art that lysis or cell destruction may result from application of shear stress to cell membranes. Red blood cells are particularly susceptible to shear stress damage as their cell membranes do not include a reinforcing cytoskeleton to maintain cell shape. Lysis of white blood cells and platelets also occurs upon application of high shear stress. Lysis of red blood cells can result in release of cell contents which trigger subsequent platelet aggregation. Sublytic shear stress leads to cellular alterations and direct activation and aggregation of platelets and white blood cells.

Several types of surgically implantable pumps have been developed in an effort to provide a mechanical device for augmenting or replacing the blood pumping action of damaged or diseased hearts. Some of these pumps are designed to support single ventricular function. Such pumps usually support the left ventricle, which pumps blood to the entire body except the lungs, since it becomes diseased far more commonly than the right ventricle, which pumps blood only to the lungs. Other devices have been tested and used for providing biventricular function.

Depending on the needs of a particular patient and the design of a pump, pumping units such as so-called "VADs" (ventricular assist devices) can be implanted to assist a functioning heart that does not have adequate pumping capability. Other types of pumps, such as the so-called "Jarvik heart," can be used to completely replace a heart which has been surgically removed.

Temporary as well as permanent implantable pumps have been developed. "Permanent" in this sense refers to the remaining life of the patient; after a patient's death, any artificial pumping device is usually removed for analysis. "Temporary" implantation usually involves (1) an attempt to reduce the stress on a heart while it recovers from surgery or some other short-term problem, or (2) use of a pump as a "bridge" to forestall the death of a patient until a suitable donor heart can be found for cardiac transplantation.

The most widely tested and commonly used implantable blood pumps employ variable forms of flexible sacks (also spelled sacs) or diaphragms which are squeezed and released in a cyclical manner to cause pulsatile ejection of blood. Such pumps are discussed in books or articles such as Hogness and Antwerp 1991, DeVries et al 1984, and Farrar et al 1988, and in U.S. Pat. Nos. 4,994,078 (Jarvik 1991), 4,704,120 (Slonina 1987), 4,936,758 (Coble 1990), and 4,969,864 (Schwarzmann et al 1990). Sack or diaphragm pumps are subject to fatigue failure of compliant elements and as such are mechanically and functionally quite different from the pump which is the subject of the present invention.

An entirely different class of implantable blood pumps uses rotary pumping mechanisms. Most rotary pumps can be classified into two categories: centrifugal pumps and axial pumps. Centrifugal pumps, which include pumps marketed by Sarns (a subsidiary of the 3M Company) and Biomedicus (a subsidiary of Medtronic, Eden Prairie, Minn.), direct blood into a chamber, against a spinning interior wall (which is a smooth disk in the Medtronic pump). A flow channel is provided so that the centrifugal force exerted on the blood generates flow.

By contrast, axial pumps provide blood flow along a cylindrical axis, which is in a straight (or nearly straight) line with the direction of the inflow and outflow. Depending on the pumping mechanism used inside an axial pump, this can in some cases reduce the shearing effects of the rapid acceleration and deceleration forces generated in centrifugal pumps. However, the mechanisms used by axial pumps can inflict other types of stress and damage on blood cells.

Some types of axial rotary pumps use impeller blades mounted on a center axle, which is mounted inside a tubular conduit. As the blade assembly spins, it functions like a fan, or an outboard motor propeller. As used herein, "impeller" refers to angled vanes (also called blades) which are constrained inside a flow conduit; an impeller imparts force to a fluid that flows through the conduit which encloses the impeller. By contrast, "propeller" usually refers to non-enclosed devices, which typically are used to propel vehicles such as boats or airplanes.

Another type of axial blood pump, called the "Haemopump" (sold by Nimbus) uses a screw-type impeller with a classic screw (also called an Archimedes screw; also called a helifoil, due to its helical shape and thin cross-section). Instead of using several relatively small vanes, the Haemopump screw-type impeller contains a single elongated helix, comparable to an auger used for drilling or digging holes. In screw-type axial pumps, the screw spins at very high speed (up to about 10,000 rpm). The entire Haemopump unit is usually less than a centimeter in diameter. The pump can be passed through a peripheral artery into the aorta, through the aortic valve, and into the left ventricle. It is powered by an external motor and drive unit.

Centrifugal or axial pumps are commonly used in three situations: (1) for brief support during cardiopulmonary operations, (2) for short-term support while awaiting recovery of the heart from surgery, or (3) as a bridge to keep a patient alive while awaiting heart transplantation. However, rotary pumps generally are not well tolerated for any prolonged period. Patients who must rely on these units for a substantial length of time often suffer from strokes, renal (kidney) failure, and other organ dysfunction. This is due to the fact that rotary devices, which must operate at relatively high speeds, may impose unacceptably high levels of turbulent and laminar shear forces on blood cells. These forces can damage or lyse (break apart) red blood cells. A low blood count (anemia) may result, and the disgorged contents of lysed blood cells (which include large quantities of hemoglobin) can cause renal failure and lead to platelet activation that can cause embolisms and stroke.

One of the most important problems in axial rotary pumps in the prior art involves the gaps that exist between the outer edges of the blades, and the walls of the flow conduit. These gaps are the site of severe turbulence and shear stresses, due to two factors. Since implantable axial pumps operate at very high speed, the outer edges of the blades move extremely fast and generate high levels of shear and turbulence. In addition, the gap between the blades and the wall is usually kept as small as possible to increase pumping efficiency and to reduce the number of cells that become entrained in the gap area. This can lead to high-speed compression of blood cells as they are caught in a narrow gap between the stationary interior wall of the conduit and the rapidly moving tips or edges of the blades.

An important factor that needs to be considered in the design and use of implantable blood pumps is "residual cardiac function," which is present in the overwhelming majority of patients who would be candidates for mechanical circulatory assistance. The patient's heart is still present and still beating, even though, in patients who need mechanical pumping assistance, its output is not adequate for the patient's needs. In many patients, residual cardiac functioning often approaches the level of adequacy required to support the body, as evidenced by the fact that the patient is still alive when implantation of an artificial pump must be considered and decided. If cardiac function drops to a level of severe inadequacy, death quickly becomes imminent, and the need for immediate intervention to avert death becomes acute.

Most conventional ventricular assist devices are designed to assume complete circulatory responsibilities for the ventricle they are "assisting." As such, there is no need, nor presumably any advantage, for the device to interact in harmony with the assisted ventricle. Typically, these devices utilize a "fill-to-empty" mode that, for the most part, results in emptying of the device in random association with native heart contraction. This type of interaction between the device and assisted ventricle ignores the fact that the overwhelming majority of patients who would be candidates for mechanical assistance have at least some significant residual cardiac function.

It is preferable to allow the natural heart, no matter how badly damaged or diseased it may be, to continue contributing to the required cardiac output whenever possible so that ventricular hemodynamics are disturbed as little as possible. This points away from the use of total cardiac replacements and suggests the use of "assist" devices whenever possible. However, the use of assist devices also poses a very difficult problem: in patients suffering from severe heart disease, temporary or intermittent crises often require artificial pumps to provide "bridging" support which is sufficient to entirely replace ventricular pumping capacity for limited periods of time, such as in the hours or days following a heart attack or cardiac arrest, or during periods of severe tachycardia or fibrillation.

Accordingly, an important goal during development of the described method of pump implantation and use and of the surgically implantable reciprocating pump was to design a method and a device which could cover a wide spectrum of requirements by providing two different and distinct functions. First, an ideal cardiac pumping device should he able to provide "total" or "complete" pumping support which can keep the patient alive for brief or even prolonged periods, if the patient's heart suffers from a period of total failure or severe inadequacy. Second, in addition to being able to provide total pumping support for the body during brief periods, the pump should also be able to provide a limited "assist" function. It should be able to interact with a beating heart in a cooperative manner, with minimal disruption of the blood flow generated by the natural heartbeat. If a ventricle is still functional and able to contribute to cardiac output, as is the case in the overwhelming majority of clinical applications, then the pump will assist or augment the residual cardiac output. This allows it to take advantage of the natural, non-hemolytic pumping action of the heart to the fullest extent possible; it minimizes red blood cell lysis, it reduces mechanical stress on the pump, and it allows longer pump life and longer battery life.

Several types of surgically implantable blood pumps containing a piston-like member have been developed to provide a mechanical device for augmenting or even totally replacing the blood pumping action of a damaged or diseased mammalian heart.

U.S. Pat. No. 3,842,440 to Karlson discloses an implantable linear motor prosthetic heart and control system containing a pump having a piston-like member which is reciprocal within a magnetic field. The piston-like member includes a compressible chamber in the prosthetic heart which communicates with the vein or aorta.

U.S. Pat. Nos. 3,911,897 and 3,911,898 to Leachman, Jr. disclose heart assist devices controlled in the normal mode of operation to copulsate and counterpulsate with the heart, respectively, and produce a blood flow waveform corresponding to the blood flow waveform of the heart being assisted. The heart assist device is a pump connected serially between the discharge of a heart ventricle and the vascular system. The pump may be connected to the aorta between the left ventricle discharge immediately adjacent the aortic valve and a ligation in the aorta a short distance from the discharge. This pump has coaxially aligned cylindrical inlet and discharge pumping chambers of the same diameter and a reciprocating piston in one chamber fixedly connected with a reciprocating piston of the other chamber. The piston pump further includes a passageway leading between the inlet and discharge chambers and a check valve in the passageway preventing flow from the discharge chamber into the inlet chamber. There is no flow through the movable element of the piston.

U.S. Pat. No. 4,102,610 to Taboada et al. discloses a magnetically operated constant volume reciprocating pump which can be used as a surgically implantable heart pump or assist. The reciprocating member is a piston carrying a tilting-disk type check valve positioned in a cylinder. While a tilting disk valve results in less turbulence and applied shear to surrounding fluid than a squeezed flexible sack or rotating impeller, the shear applied may still be sufficiently excessive so as to cause damage to red blood cells.

U.S. Pat. Nos. 4,210,409 and 4,375,941 to Child disclose a pump used to assist pumping action of the heart having a piston movable in a cylindrical casing in response to magnetic forces. A tilting-disk type check valve carried by the piston provides for flow of fluid into the cylindrical casing and restricts reverse flow. A plurality of longitudinal vanes integral with the inner wall of the cylindrical casing allow for limited reverse movement of blood around the piston which may result in compression and additional shearing of red blood cells. A second fixed valve is present in the inlet of the valve to prevent reversal of flow during piston reversal.

U.S. Pat. No. 4,965,864 to Roth discloses a linear motor using multiple coils and a reciprocating element containing permanent magnets which is driven by microprocessor-controlled power semiconductors. A plurality of permanent magnets is mounted on the reciprocating member. This design does not provide for self-synchronization of the linear motor in the event the stroke of the linear motor is greater than twice the pole pitch on the reciprocating element. During start-up of the motor, or if magnetic coupling is lost, the reciprocating element may slip from its synchronous position by any multiple of two times the pole pitch. As a result, a sensing arrangement must be included in the design to detect the position of the piston so that the controller will not drive it into one end of the closed cylinder. In addition, this design having equal pole pitch and slot pitch results in a "jumpy" motion of the reciprocating element along its stroke.

In addition to the piston position sensing arrangement discussed above, the Roth design may also include a temperature sensor and a pressure sensor as well as control circuitry responsive to the sensors to produce the intended piston motion. For applications such as implantable blood pumps where replacement of failed or malfunctioning sensors requires open heart surgery, it is unacceptable to have a linear motor drive and controller that relies on any such sensors. In addition, the Roth controller circuit uses only NPN transistors thereby restricting current flow to the motor windings to one direction only.

U.S. Pat. No. 4,541,787 to Delong describes a pump configuration wherein a piston containing a permanent magnet is driven in a reciprocating fashion along the length of a cylinder by energizing a sequence of coils positioned around the outside of the cylinder. However, the coil and control system configurations disclosed only allow current to flow through one individual winding at a time. This does not make effective use of the magnetic flux produced by each pole of the magnet in the piston. To maximize force applied to the piston in a given direction, current must flow in one direction in the coils surrounding the vicinity of the north pole of the permanent magnet while current flows in the opposite direction in the coils surrounding the vicinity of the south pole of the permanent magnet. Further, during starting of the pump disclosed by Delong, if the magnetic piston is not in the vicinity of the first coil energized, the sequence of coils that are subsequently energized will ultimately approach and repel the magnetic piston toward one end of the closed cylinder. Consequently, the piston must be driven into the end of the closed cylinder before the magnetic poles created by the external coils can become coupled with the poles of the magnetic piston in attraction.

U.S. Pat. No. 4,610,658 to Buchwald et al. discloses an implantable fluid displacement peritoneovenous shunt system. The system comprises a magnetically driven pump having a spool piston fitted with a disc flap valve.

U.S. Pat. No. 5,089,017 to Young et al. discloses a drive system for artificial hearts and left ventricular assist devices comprising one or more implantable pumps driven by external electromagnets. The pump utilizes working fluid, such as sulfur hexafluoride to apply pneumatic pressure to increase blood pressure and flow rate.

SUMMARY OF THE INVENTION

This invention provides a connecting arrangement for connecting a medical device to a vessel in a human body including a metal ring, and a two-part sewing ring having an endothelial promoting outer covering and a compliant inner layer connected at one end to the metal ring and connectable at the other end to a vessel in the human body.

BRIEF DESCRIPTION OF THE DRAWINGS

Further objects and advantages of the invention will be apparent from a reading of the following description in conjunction with the accompanying drawings, in which.

DESCRIPTION OF PREFERRED EMBODIMENTS

Figure 1:
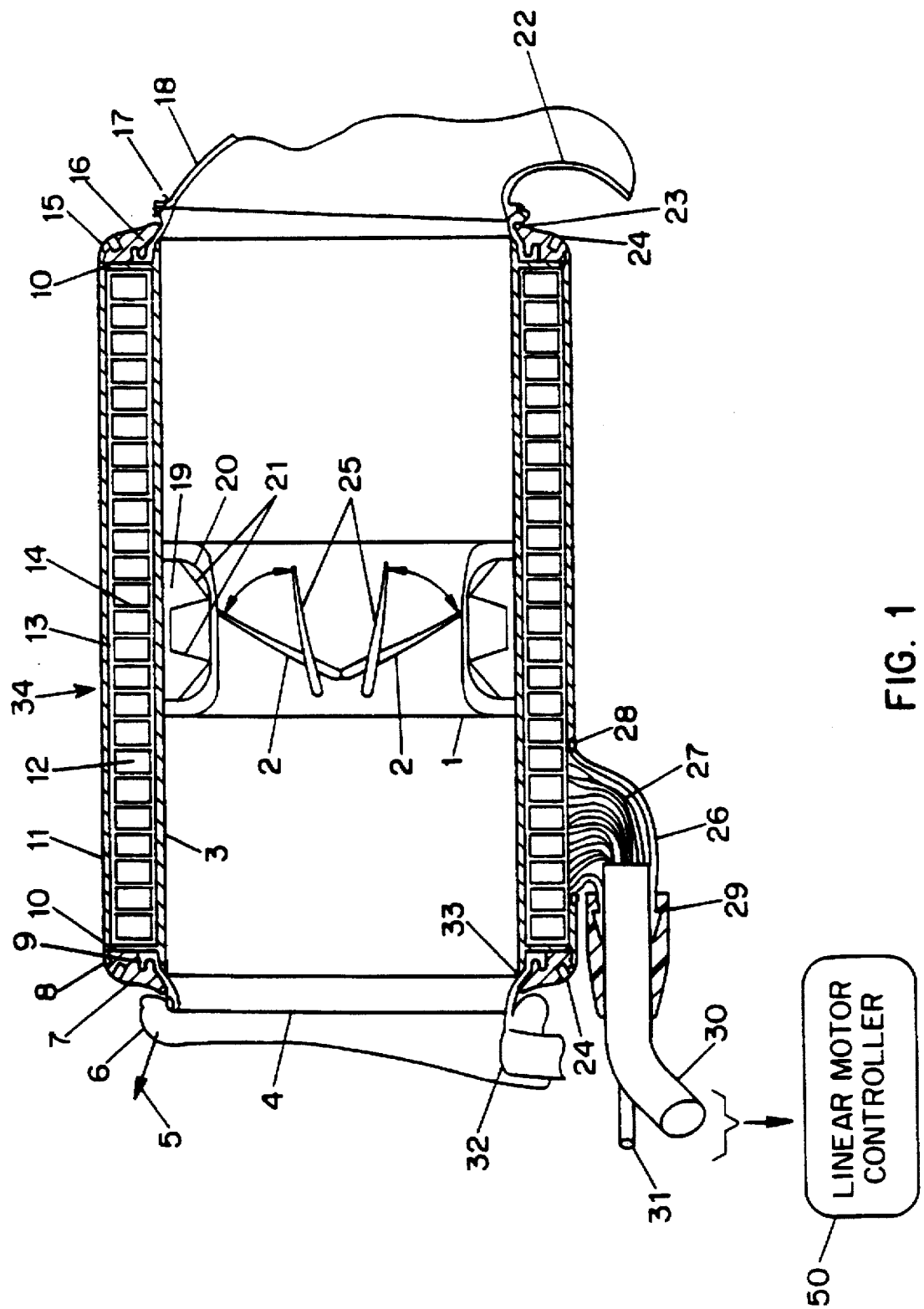
FIG. 1 is a longitudinal sectional view illustrating a representative surgically implantable pump with a reciprocating piston-valve arranged in accordance with the invention.

In the representative embodiment of a pump according to the invention as shown in FIG. 1, a pump module arrangement 34, which is for example, no more than 6 cm in diameter and 7.5 cm long, includes a reciprocating piston-valve assembly 1 consisting of an annular piston with a central flow passage containing two pivoting valve leaflets 2 which act as a check valve to limit flow through the central passage during reciprocation to one direction only. The piston-valve assembly 1 is driven back and forth through an internal cylinder 3 in the pump module 34 to displace fluid from an inlet end to an outlet end. Smooth and vibration-free motion can be ensured by providing close-clearance, low friction interfaces between the cylinder inner diameter and the piston-valve.

The piston-valve 1, leaflets 2 and internal cylinder 3 are all preferably fabricated from highly corrosion-resistant material such as titanium or carbon, and are coated with low-friction, wear-resistant, non-thrombogenic material. One material which has been shown to have a good combination of biocompatibility and high strength is pyrolytic carbon, which is used to coat the housing and leaflets of various types of prosthetic heart valves, such as the St. Jude valve. The coating can be applied by a conventional vapor deposition process, resulting in a layer containing about 90% carbon and 10% silicon on the surface of a graphite structure.

When used as an implantable left ventricular assist device (LVAD), the pump module 34 is attached at its inlet end using a sewing cuff 4 to a patient's aorta 5 immediately downstream of the aortic valve (not shown in FIG. 1) using a suture 6. In this manner, the patient's own normally functioning aortic valve precludes back-flow of blood into the patient's left ventricle when the piston-valve makes its return stroke. Preferably the sewing cuff 4 is made from a synthetic surgical graft material such as woven Dacron™ available from the Dupont Corporation. The sewing cuff 4 can be attached to the LVAD using a retaining ring 7 which snaps into cantilevered barbs 8 or other similar retaining arrangements. The sewing cuff has an enlarged end 9 which becomes physically captured or entrapped by the retaining ring 7 when it is snapped into place. Compression of the sewing cuff 9 by the retaining ring 7 against the cylinder 3 forms a hemostatic seal.

At the outlet end of the cylinder 3 a retaining ring 15 is used in conjunction with a sewing cuff 16 in a similar manner as described herein above. The sewing cuff 16 is attached using a suture 17 to the patient's distal ascending aorta 18.

If the pump is to be inserted directly into an artery, the sewing cuffs 4 and 16 should be relatively short, such as about 2 cm or less in length. If the pump is designed for insertion in any other manner, such as for direct left atrial-to-aortic ventricular assistance in which an opening is cut into a wall of the left atrium and directly into the aorta, bypassing the left ventricle, the sewing cuffs should be substantially longer, such as about 30 cm or more at each end so they can be cut to any designed length by a surgeon without requiring an additional suturing procedure for an attachment cannula.

Figure 2:
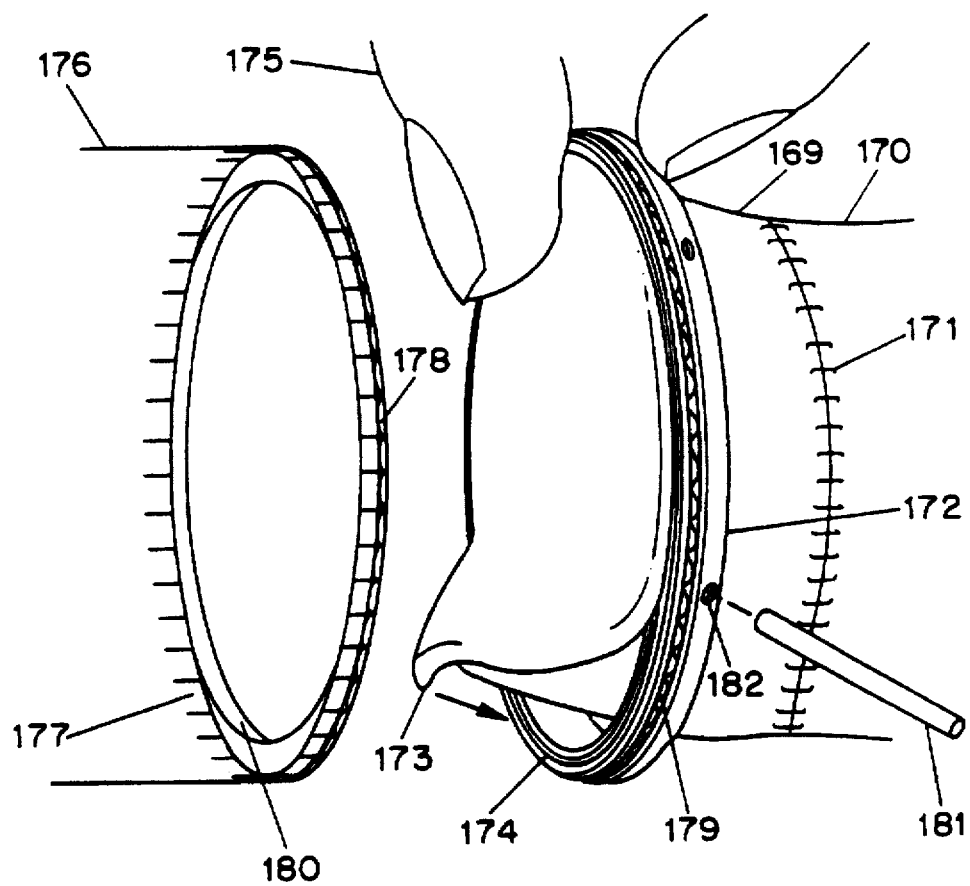
FIG. 2 is a perspective view illustrating a representative arrangement for attachment of vascular grafts to a surgically implantable pump in accordance with the invention.

FIG. 2 depicts a method and arrangement for attachment of vascular grafts to a surgically implantable pump module 176. A graft 169 is sewn to a patient's native vessel 170 using a suture 171. The suturing is performed prior to the installation of a retaining ring 172 which is not permanently attached to the graft 169, thereby avoiding obstruction by the retaining ring while suturing. The retaining ring 172 is installed onto the graft 169 after suturing is completed by slipping the retaining ring over the flexible graft and inserting an enlarged lip 173 of the graft into a recessed groove 174 using the thumb and forefinger 175 as shown. The enlarged lip may optionally be seated against a simple shoulder inside the retaining ring, instead of the recessed groove 174. After the graft is properly seated in the retaining ring 172, a pump module 176 is fastened to the retaining ring using cantilevered springs 177 extending from the pump module 176 which incorporate barbs 178. These barbs seat and lock axially into mating recesses 179 machined into the retaining ring 172. Alternate fastening arrangements may also be used such as a "bayonet" type connection, which is commonly used in cylindrical electrical connectors and involves the use of locking cams and spring loaded followers. Once seated, the graft forms a hemostatic seal around a hollow extension 180 of the internal cylinder in the pump module. The retaining ring can be removed by inserting a bar 181 or other engaging device into equally-spaced holes 182 in the ring and rotating the ring 172 slightly. For the fastening arrangement shown, this will cause the barbs 178, which are rounded when viewed in a circumferential cross-section, to ride up and out of the recesses 179, disengaging the axial locking feature and permitting the retaining ring to be removed. Instead of the bar 181, a more sophisticated spanner wrench type tool can be used.

Figure 2A:
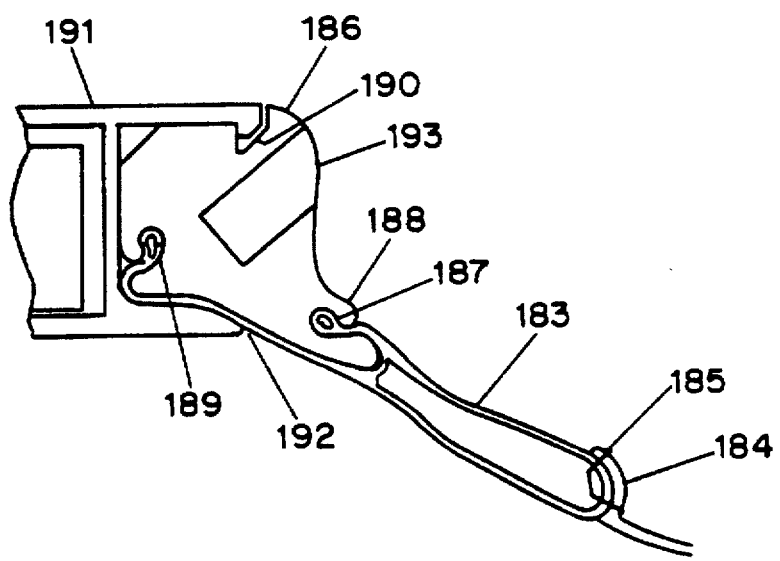
FIG. 2(a) is an enlarged fragmentary view illustrating another alternative arrangement for attachment of the pump to a blood vessel.

An alternate graft configuration is shown in FIG. 2(a). In this case, a sewing ring 183 is attached to an artery 184 using a two-layered suturing technique (not shown). The cuff is filled with foam or other filler material to ease suture attachment by producing a thicker graft as shown. The graft 183 can be directly attached to a retaining ring 186 or, if desired, it can be attached to the retaining ring by an intervening thinner graft material 169 of the type shown in FIG. 2. Conversely, a thicker graft 183 may be attached by using an enlarged lip of graft material 173 inserted into a groove similar to the groove 174 shown in FIG. 2 if access to a suture line 185 is considered to be inadequate with the retaining ring 186 preattached to the graft 183. In one method of attaching the graft 183 to the retaining ring 186, an enlarged lip 187 of the graft is inserted into a groove 188 machined in the retaining ring and then mechanically rolled within the groove which physically captures the end of the graft. A similar enlarged lip 189 can be rolled within a groove on the inside of the retaining ring. An alternate method of attaching the graft such as a separate metallic ring compressed around the graft may also be used instead of the rolled-over lips 187 and 189.

The retaining ring 186 has a series of recesses 190 shaped to conform to the inside surfaces of barbed cantilevered springs 191. The sectional view of FIG. 2(a) shows a spring 191 and a recess 190 corresponding to the springs 177 and recesses 179, discussed above with respect to FIG. 2, by which the retaining ring is assembled to the pump module. The clearance between the retaining ring 172 or 186 and the pump module when they are assembled is such that the spring 177 or 191 presses radially inwardly and slightly axially on the retaining ring, thereby compressing the graft 173 or 183 against the inner cylinder extension 180 or 192 to form a hemostatic seal. As in the embodiment of FIG. 2, the recesses 190 are shaped so that the retaining ring 186 can be released by inserting a tool in one or more equally spaced holes.

Figure 3:
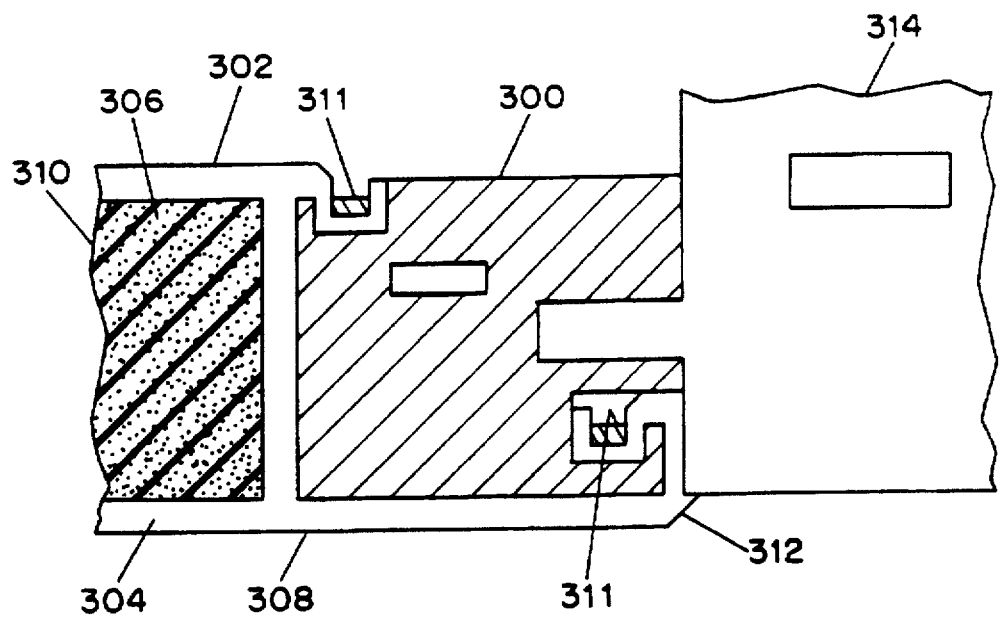
FIG. 3 is an enlarged fragmentary sectional view illustrating a representative quick connect locking system for attaching a surgically implantable pump with a blood vessel arranged in accordance with the invention.

In another preferred embodiment, the aorta-pump connection is obtained using a quick connect locking system as shown in FIG. 3. The quick connect locking system comprises a metal ring 300 of titanium or other suitable metal and a sewing ring 302. The sewing ring includes a dacron endothelial promoting outer covering 304 and compliant foam rubber inner part 306. One end 308 of the sewing ring 302 is attached to the metal ring 300 by any connecting arrangement compatible with human implantation, for example, by internal circumferential fastener bands 311. The metal ring 300 is, in turn, coupled to a pump module 314 by one of the quick connect locking mechanisms of the type discussed above which is shown schematically in FIG. 3. The other end 310 of the sewing ring 302 is sutured to the aorta in the usual manner. The suture connection anastomosis will smooth over with time as endothelium from the native aorta extends over the outer covering 304. The endothelial overgrowth 312 will also extend over the junction of the quick connect locking mechanism.

Returning to the pump arrangement shown in FIG. 1, a high energy density rare earth permanent magnet 19 having axially spaced north and south pole pieces 21 is mounted on the circumference of the piston-valve 1. A hermetically sealed enclosure 20 made from a highly corrosion-resistant material such as titanium surrounds the permanent magnet 19 and its pole pieces 21. Preferably, the high energy density rare earth material is neodymium-iron-boron. The pole pieces 21, which are made from soft ferromagnetic material, direct the magnetic flux so as to project outward radially from the axially oriented permanent magnet toward the circumference of the piston-valve. The radial magnetic flux thus intercepts the windings 12 of a linear motor that surrounds the cylinder 3 through which the piston-valve 1 slides, the windings being formed in slots separated by magnetically soft lamination material 14 of the type commonly used in commercial motors, generators and transformers. A magnetically soft backing 13 surrounds the winding slots to provide a low reluctance path for the flux generated by the piston-valve magnet to link the windings. The laminations are positioned so as to avoid slot harmonics which would cause non-uniform motion of the piston-valve and are sized to minimize the effective air gap across which the magnetic flux must pass. Particularly smooth motion is obtained by using odd/even ratios of winding slot pitch to magnetic pole pitch on the piston-valve, respectively, or vice versa. In this regard, multiple phase windings are required.

The linear motor windings and laminations are encased in a corrosion-resistant enclosure which includes a hermetically sealed penetration 26 for a linear motor lead bundle 30 leading to a linear motor controller 50 described hereinafter. This bundle further includes a pair of epicardial sensing leads 31. A seal weld 10 is provided at each end of the pump module 34 to form a hermetic seal between an outer housing 11 for the pump and the inner cylinder 3. The hermetic seal prevents moisture or other contaminants from attacking the linear motor windings 12, back iron material 13 or lamination material 14.

Suitable voltage is provided to the windings of the linear motor by wires in the bundle 30 which are connected to a battery associated with the controller 50. The wires which supply power to the motor are positioned outside the aorta and thus do not contact blood flowing through the aorta.

The outer housing 11 can be composed of any suitably hard biocompatible material, such as titanium, stainless steel, various other alloys, graphite, or plastic. It can be sealed with a standard waterproof epoxy coating.

In operation, as the piston-valve 1 moves toward the outlet end of the pump, i.e., the right end as viewed in FIG. 1, fluid on the downstream side of the piston-valve is ejected from the outlet end due to the fact that the piston-valve leaflets automatically move to their closed position 2 from their open position 25 shown in dotted lines when the piston-valve moves with respect to the fluid in the pump toward the outlet end of the pump or when fluid attempts to flow past the piston-valve in the direction toward the inlet. As the piston-valve 1 reaches the outlet end of its pumping stroke, its direction of travel is reversed by the controller 50 and, as the piston-valve begins its travel back toward the inlet end of the cylinder, i.e., the left end as viewed in FIG. 1, the piston-valve leaflets automatically move to the open position 25, allowing the fluid to flow from the upstream side of the piston-valve to the downstream side of the piston-valve as it moves along the cylinder.

If the linear motor malfunctions and attempts to drive the piston-valve beyond the ends of the cylinder 3, the retaining rings 7 and 15 are shaped so as to prevent the piston-valve from moving past the sewing cuffs 4. As another back-up mechanism, the shape of the retaining rings 7 and 15 is arranged so that the piston-valve will not become jammed in the sewing cuff or damage the sewing cuff in any way. In the outlet end of the pump used as a LVAD, a patient's aorta 32 bends sharply at the aorta arch 22. To smooth out the flow path, the retaining ring 15 may have a trimmed portion 23 at this location as shown in FIG. 1. The retaining rings 7 and 15 preferably have at least four equally spaced tool holes 24 to receive a tool for removing the retaining rings after they have been snapped into place as described above.

In LVAD applications, where the pump is positioned in the outflow duct of the left ventricle, the pump inlet is downstream of the left and right coronary artery ostia or openings. During normal operation, the piston travels back from the outlet end of the cylinder as slowly as possible during the patient's native heart diastole so that it arrives at the inlet end of the cylinder just before the patient's left ventricle begins to eject blood during systole. This ensures that the patient's coronary artery 32 receives adequate blood flow during diastole, when most of the blood that normally enters the coronary arteries is actually admitted. The slow motion of the piston-valve back toward the inlet end of the cylinder also limits shear stress in the blood flowing to the downstream side of the piston-valve and should result in a slight increased pressure at the inlet to the patient's coronary arteries, which will improve blood flow to the patient's native heart muscle during diastole. This is expected to compensate for the possibly slightly reduced pressure at the inlet to the patient's coronary arteries that will occur during systole caused by the pumping action of the piston-valve moving toward the outlet end of the cylinder. A seam 33 formed at the interfaces between each of the sewing cuffs 4 and 16 and the hollow cylinder 3 is compressed against the cylinder by the retaining rings 7 and 15. This ensures that the crevice formed at the seam will become covered with a smooth secure endothelial layer to preclude formation and release of blood clots in this area.

The hermetically sealed cable penetration 26 which is made from a highly corrosion-resistant material such as titanium houses the linear motor winding leads 27 and is seal welded to the outer housing 11. The main lead bundle 30 contains a shielded multi-conductor cable with a polyurethane jacket material similar to insulation currently used for pacemaker leads. Such cable is commercially available for machine tool and robotics application, and is rated in excess of 6 million bend cycles from straight to its minimum bend radius without failure of the insulation or conductors. The main lead bundle incorporates approximately 24 conductors required to drive the linear motor in VAD applications. The main lead bundle terminates at a hermetically sealed cylindrical connector at the linear motor controller 50. A molded polyurethane strain relief 29 attaches the polyurethane jacket of the shielded multi-conductor cable 30 which constitutes the main lead bundle to the linear motor to the cable penetration. An optional second strain relief attached to the polyurethane jacket includes the leads 31 which are routed to epicardial electrodes used to provide an ECG signal to the linear motor controller 50.

Figure 4:
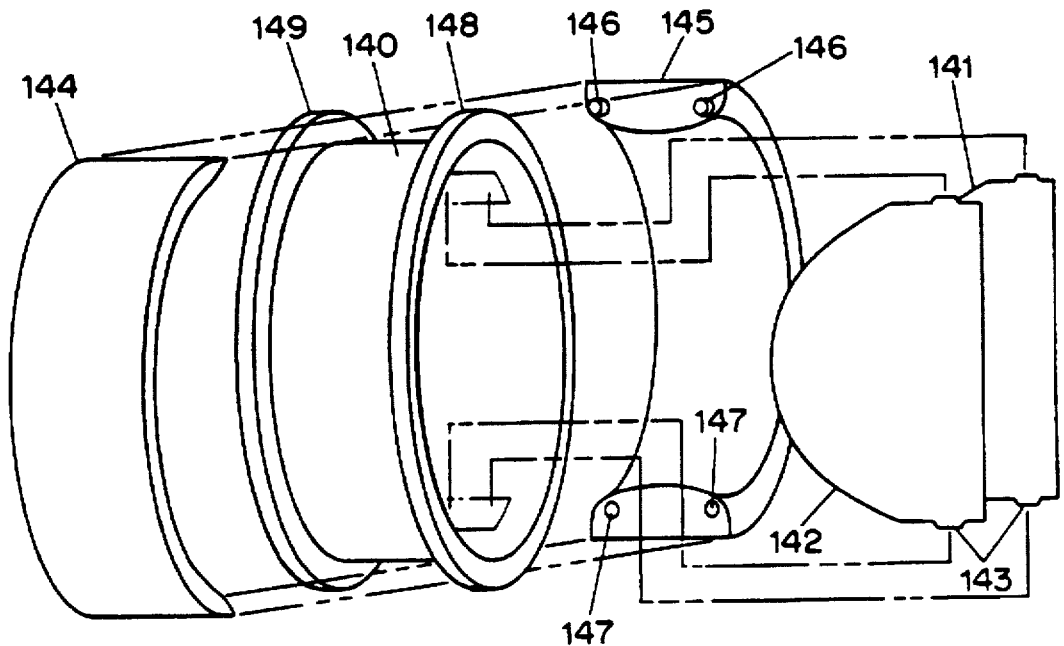
FIG. 4 is an exploded perspective view showing the arrangement of a typical piston-valve for use in a surgically implantable pump in accordance with the invention.
Figure 17:
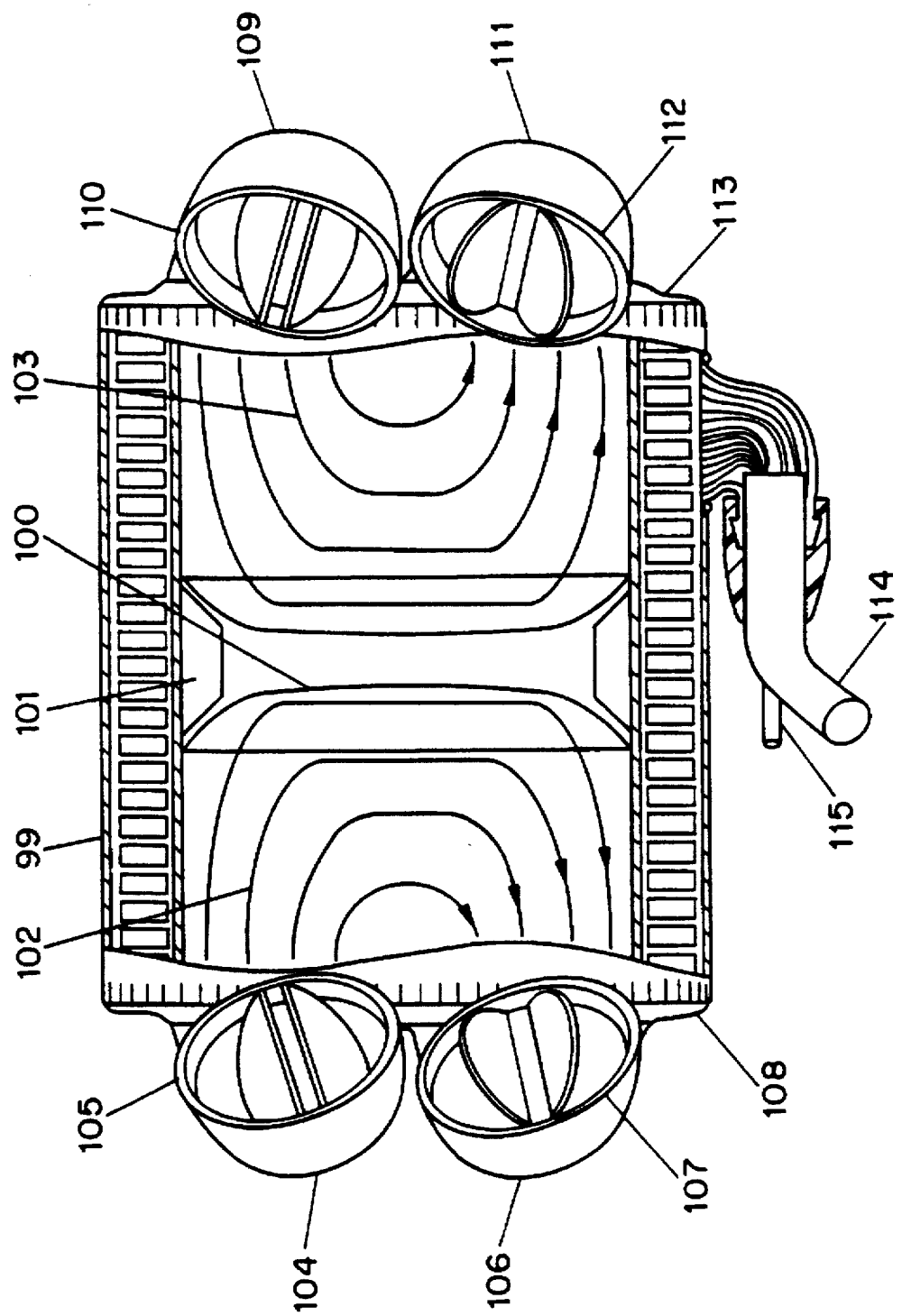
FIG. 17 is a longitudinal sectional view showing a surgically implantable pump arranged in accordance with the invention and configured as a simplex total artificial heart.
Figure 18:
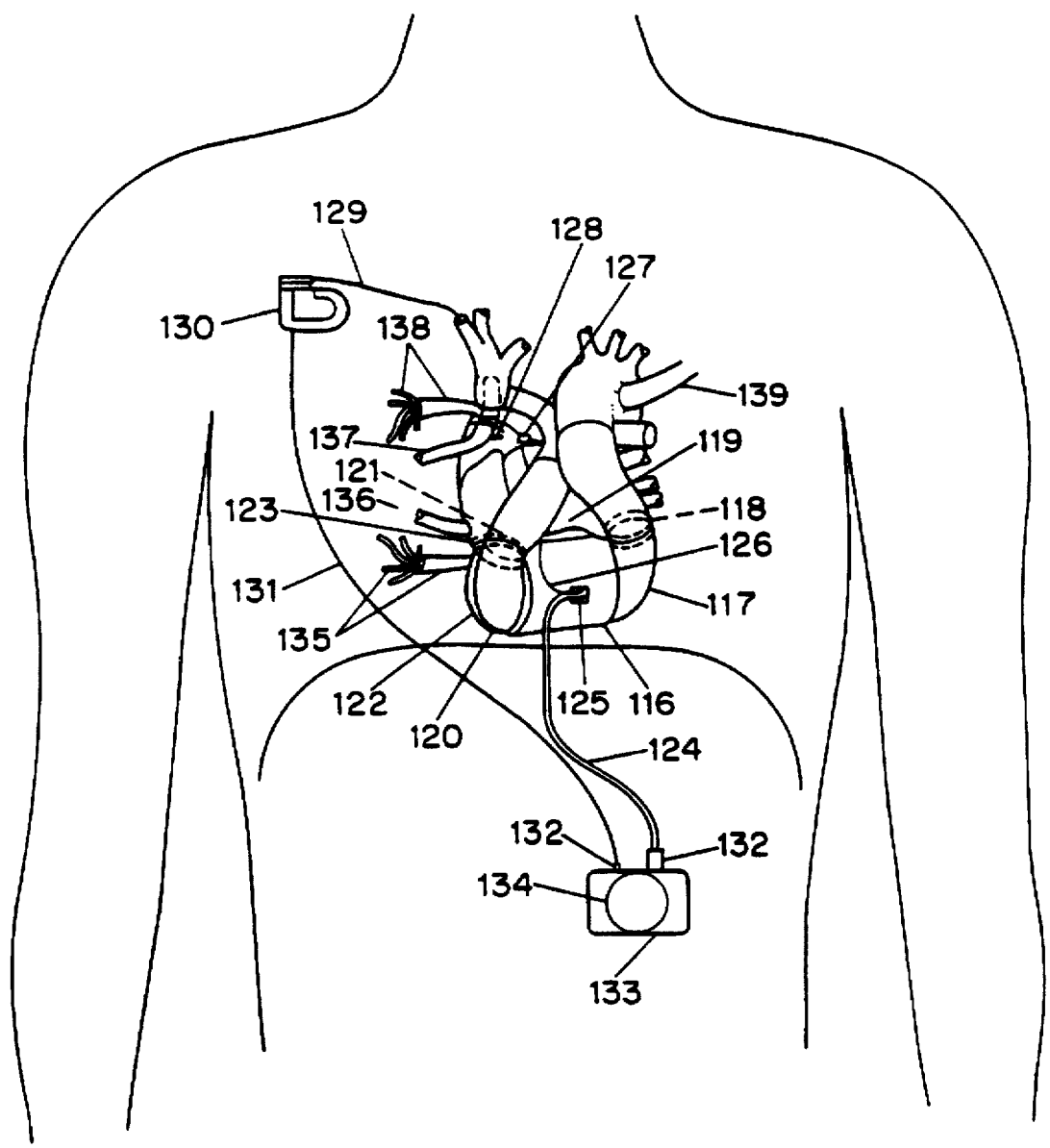
FIG. 18 is a schematic illustration showing the anatomical arrangement of the surgically implantable pump shown in FIG. 17 implanted in a simplex total artificial heart configuration.

FIG. 4 shows a representative piston-valve structure for use in the surgically implantable pumps discussed herein. The piston body has a main carrier 140 constructed of a light weight wear- and corrosion-resistant material such as titanium, silicon carbide or graphite, appropriately coated with a biocompatible material such as pyrolytic carbon. For the simplex TAH embodiment shown in FIG. 17, the piston body has a carrier which is solid, whereas in the embodiment shown in FIG. 4 the carrier 140 has a central opening in which valve leaflets 141 and 142 are inserted to form a check valve similar to those used for prosthetic heart valves. To support the leaflets 141 and 142, the carrier opening has small depressions into which leaflet hinge tabs 143 are inserted by thermally or otherwise expanding the carrier such that the tabs 143 will clear the inner dimensions of the orifice, and then allowing the carrier to contract around the leaflets, resulting in mechanical retention of the tabs in their corresponding depressions.

The magnet assemblies 144 and 145 are preferably mounted around the carrier 140 after the leaflets 142 and 143 are installed. This avoids exposure of the magnets to the potentially high temperatures which may be experienced during leaflet insertion or application of the biocompatible coating which may be pyrolytic carbon. Each magnet assembly contains one or more high energy density permanent magnets, and appropriate pole pieces to direct the flux outward radially, all hermetically sealed within a corrosion-resistant covering. Each magnet assembly consists of two halves 144 and 145 provided with insertion studs 146 and stud receivers 147 or other arrangements for fastening the two magnet assembly halves securely around the carrier when they are pressed together. A biocompatible adhesive compound may also be used to provide additional security to the assembly of the magnet halves 144 and 145. When assembled to the carrier 140, the outer surface of the magnet halves 144 and 145 is slightly recessed with respect to the outermost rim surfaces 148 and 149 of the carrier. This ensures that only the surfaces 148 and 149, which are precision machined wear surfaces, are in contact with the cylinder walls of the pump module as the piston travels through its stroke.

Figure 5:
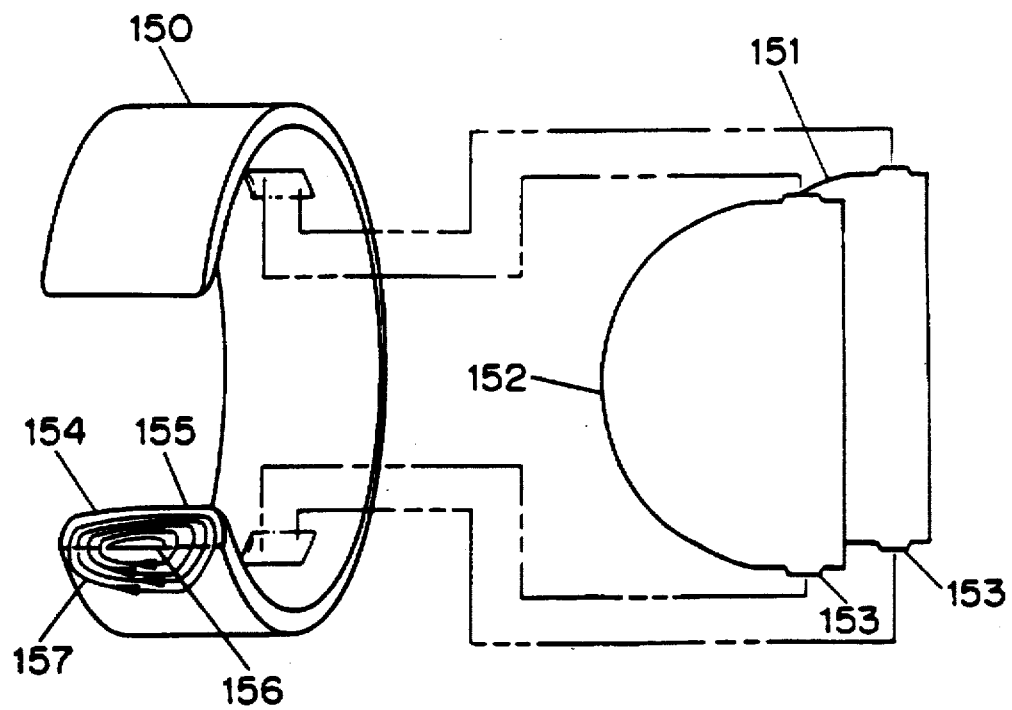
FIG. 5 is an exploded view showing an alternate configuration for assembling a piston-valve for use in a surgically implantable pump in accordance with the invention.

FIG. 5 shows an alternate embodiment of a piston-valve assembly. In this embodiment, a carrier 150 is solid and has a central opening as shown for insertion of valve leaflets 151 and 152, or other arrangements to form a valve similar to conventional prosthetic heart valves. The leaflets incorporate tabs 153 to be inserted into corresponding depressions in the central opening of the carrier by thermally or otherwise expanding the carrier. In this piston configuration, two magnets 154 and 155 are incorporated into the carrier and are manufactured to have the desired shape of the carrier, less the biocompatible coating. A spacer 156 may also be included to produce the desired carrier shape. The magnets are preferably oriented to provide the required flux pattern 157 so that pole pieces are not required. Although this piston-valve configuration may require that the magnet material be exposed to the high temperatures potentially experienced during coating application and leaflet insertion, the magnet material should not lose its preferential grain orientation provided the sintering temperature of the magnetic material is not exceeded. If the Curie temperature of the magnet material is approached or exceeded, however, the magnet may require remagnetization.

Figure 6:
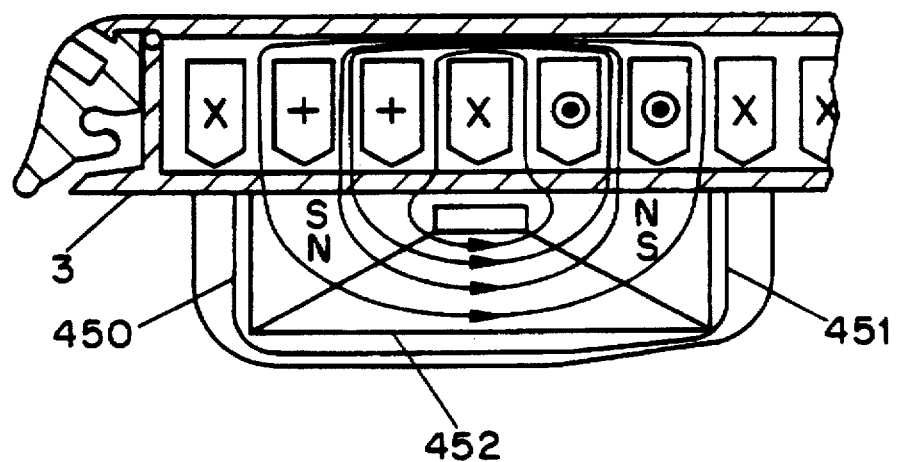
FIG. 6 is a fragmentary cross-sectional view showing an alternate magnet arrangement for use in a surgically implantable pump in accordance with the invention.
Figure 7I:
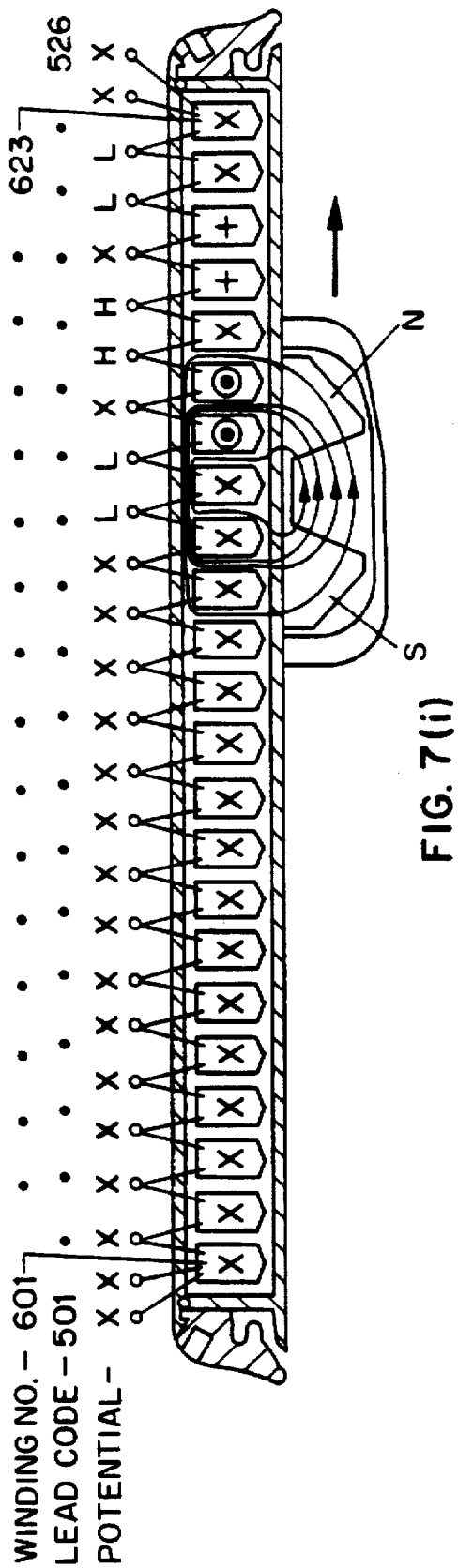
FIGS. 7(a)–7(f) are fragmentary cross-sectional views illustrating the stages in the energization of the coils of a linear motor drive in accordance with the invention.
Figure 7J:
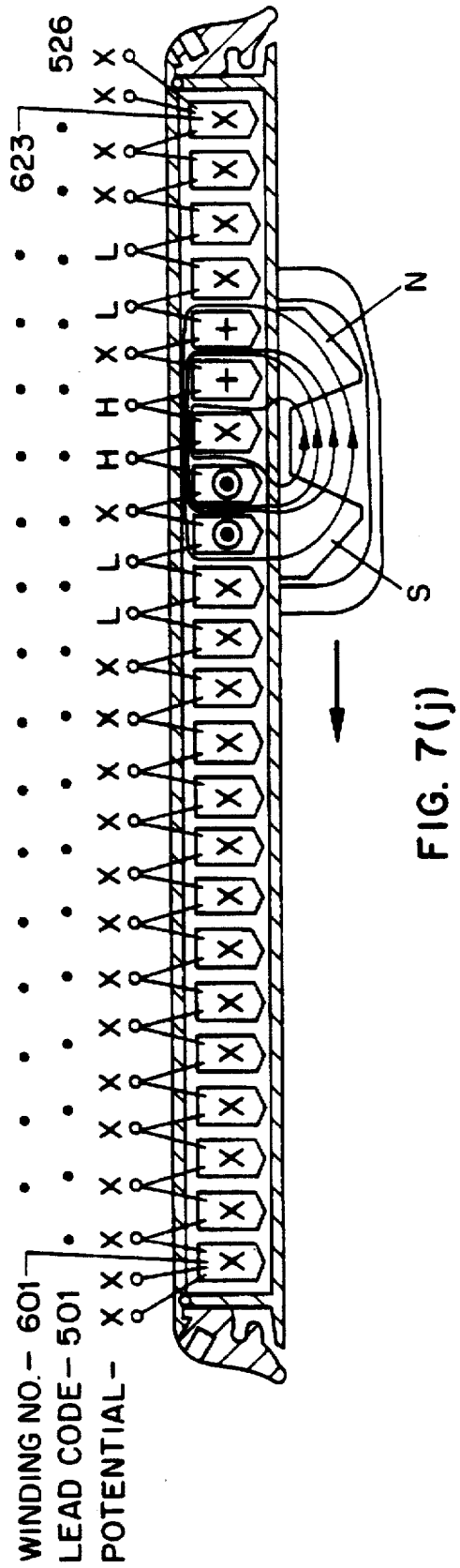
Figure 8:
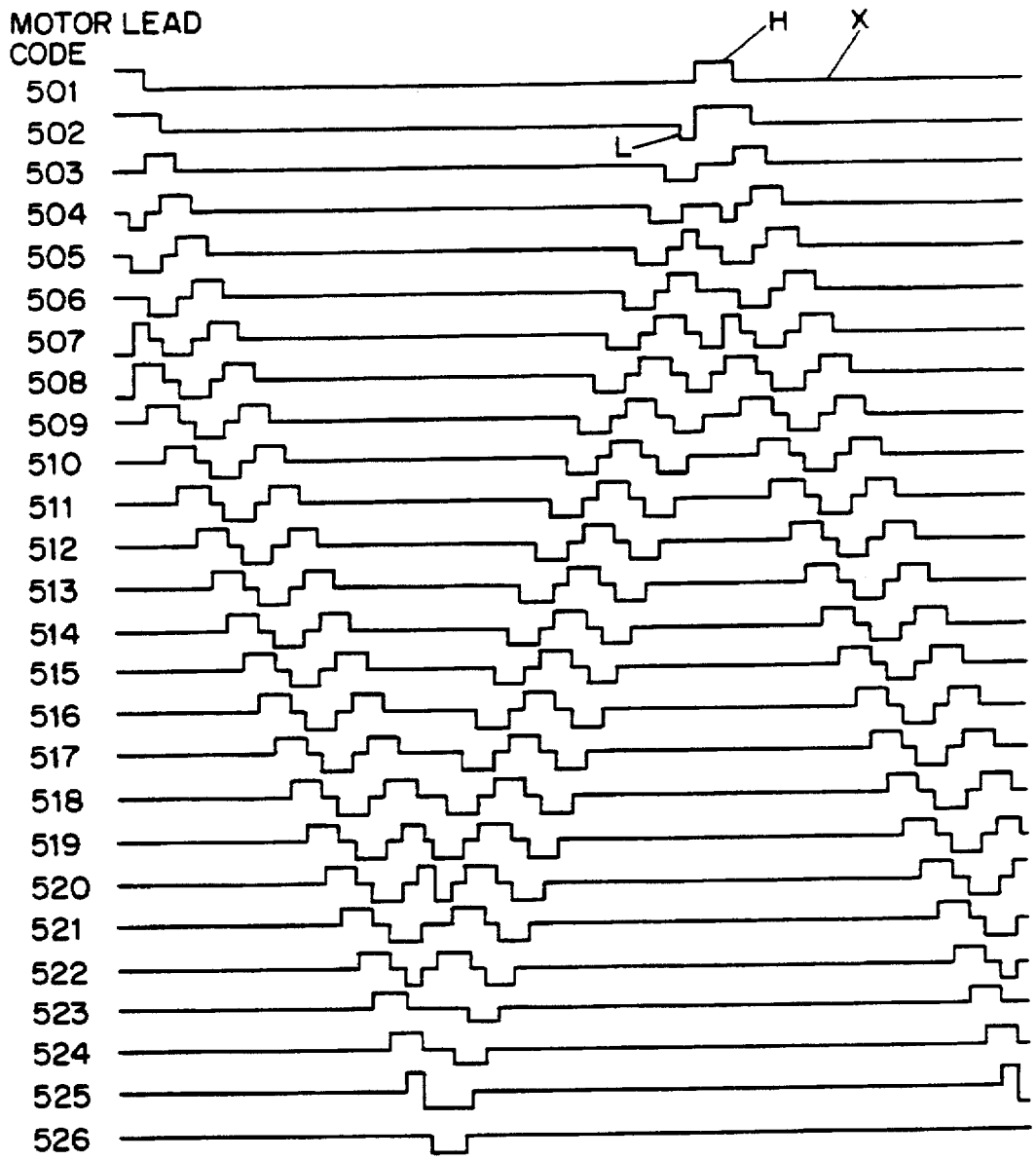
FIGS. 8 and 8(a) are graphical representatives showing the timing of the application potential to the coils of the linear motor of FIG. 1 in accordance with the invention and a typical electrocardiogram signal respectively.
Figure 8A:
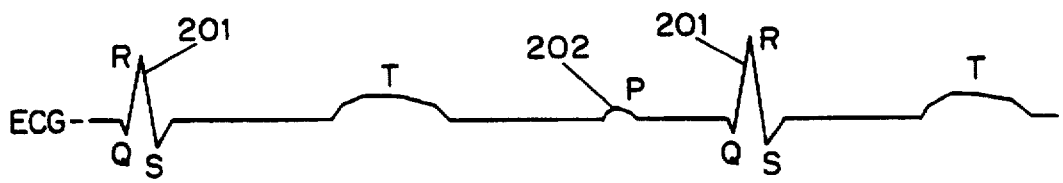
Figure 9A:
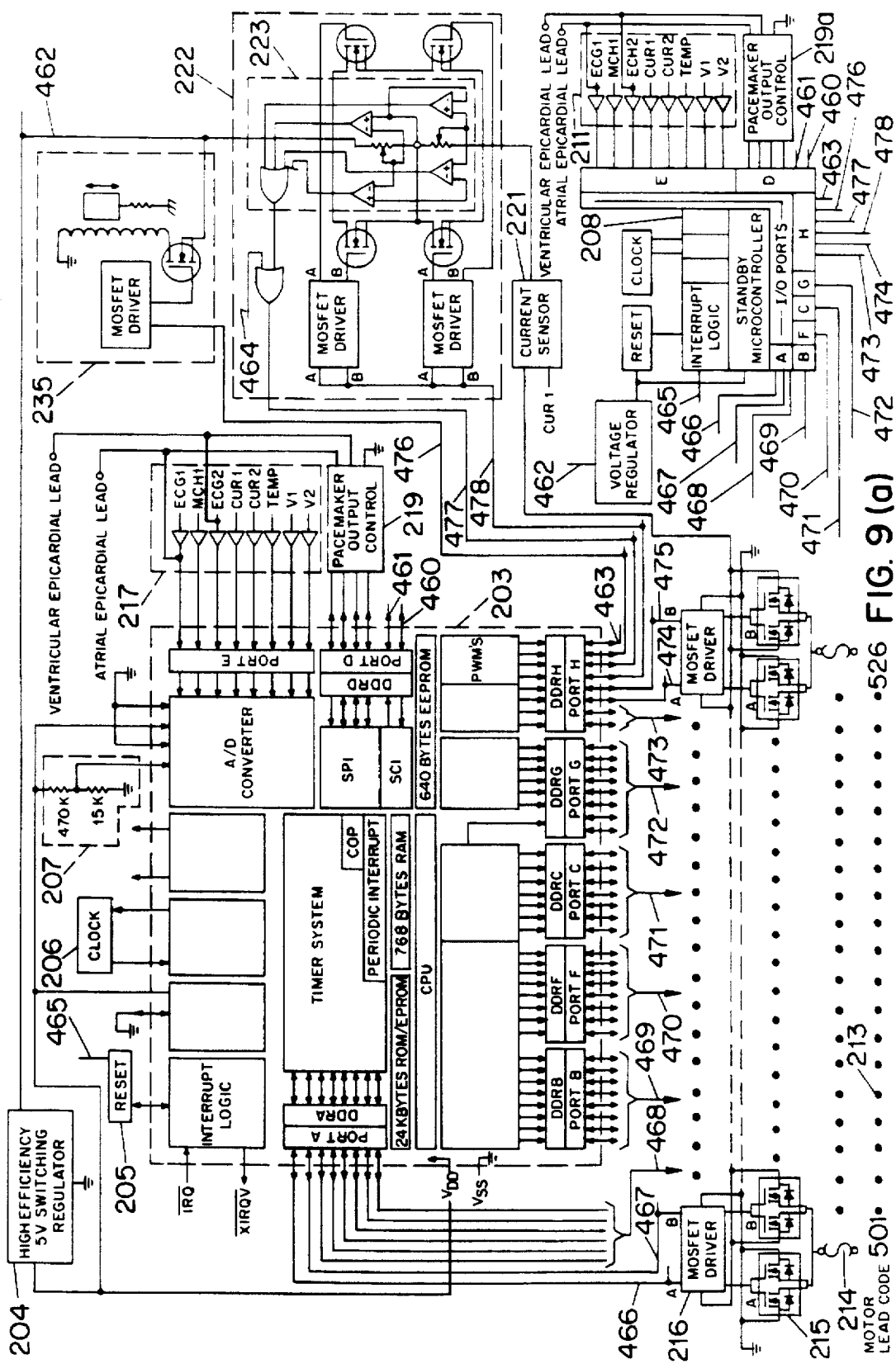
FIGS. 9(a)–9(c) are schematic circuit diagrams of a controller circuit in accordance with the invention.
Figure 9B:
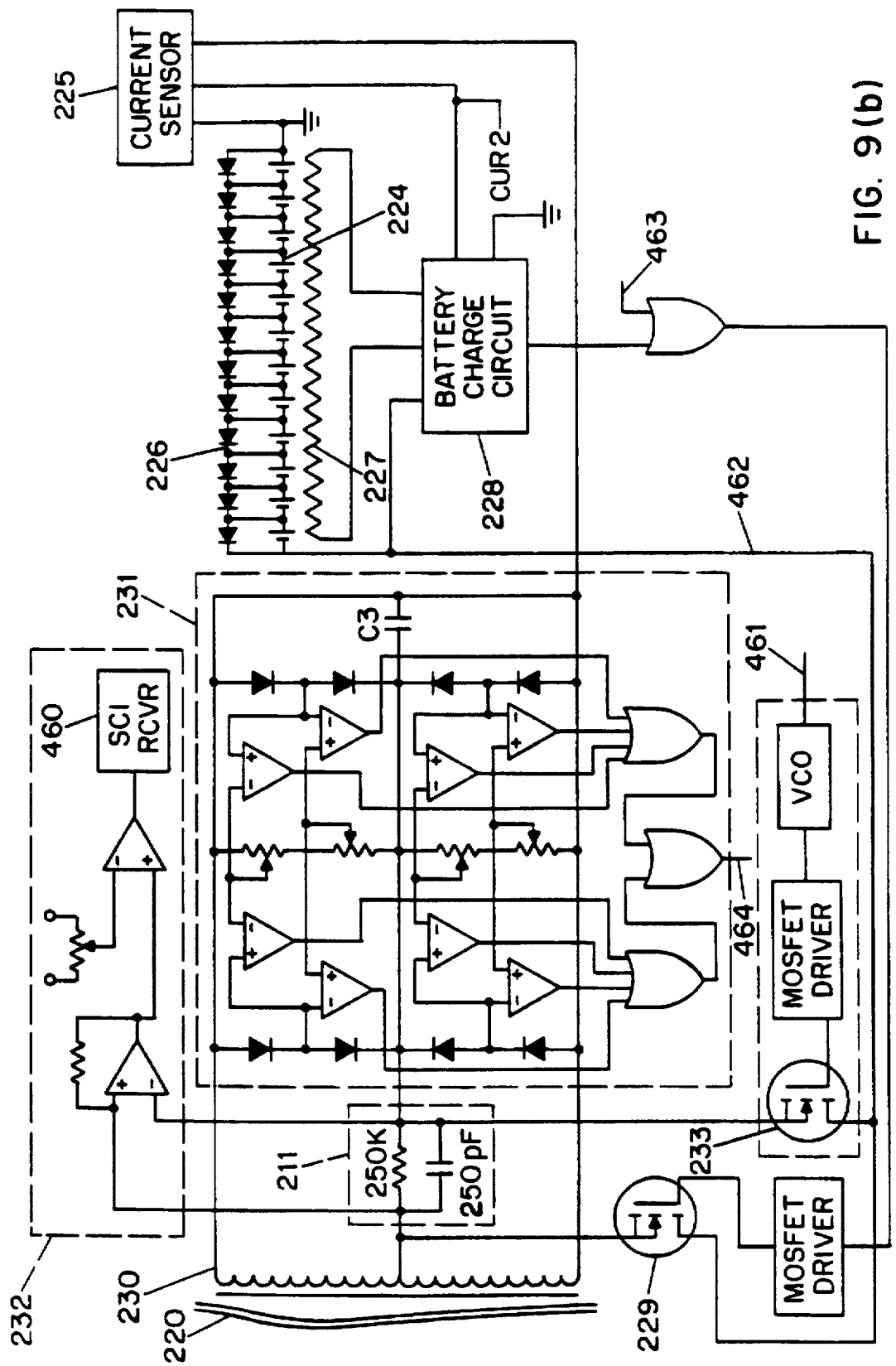
Figure 9C:
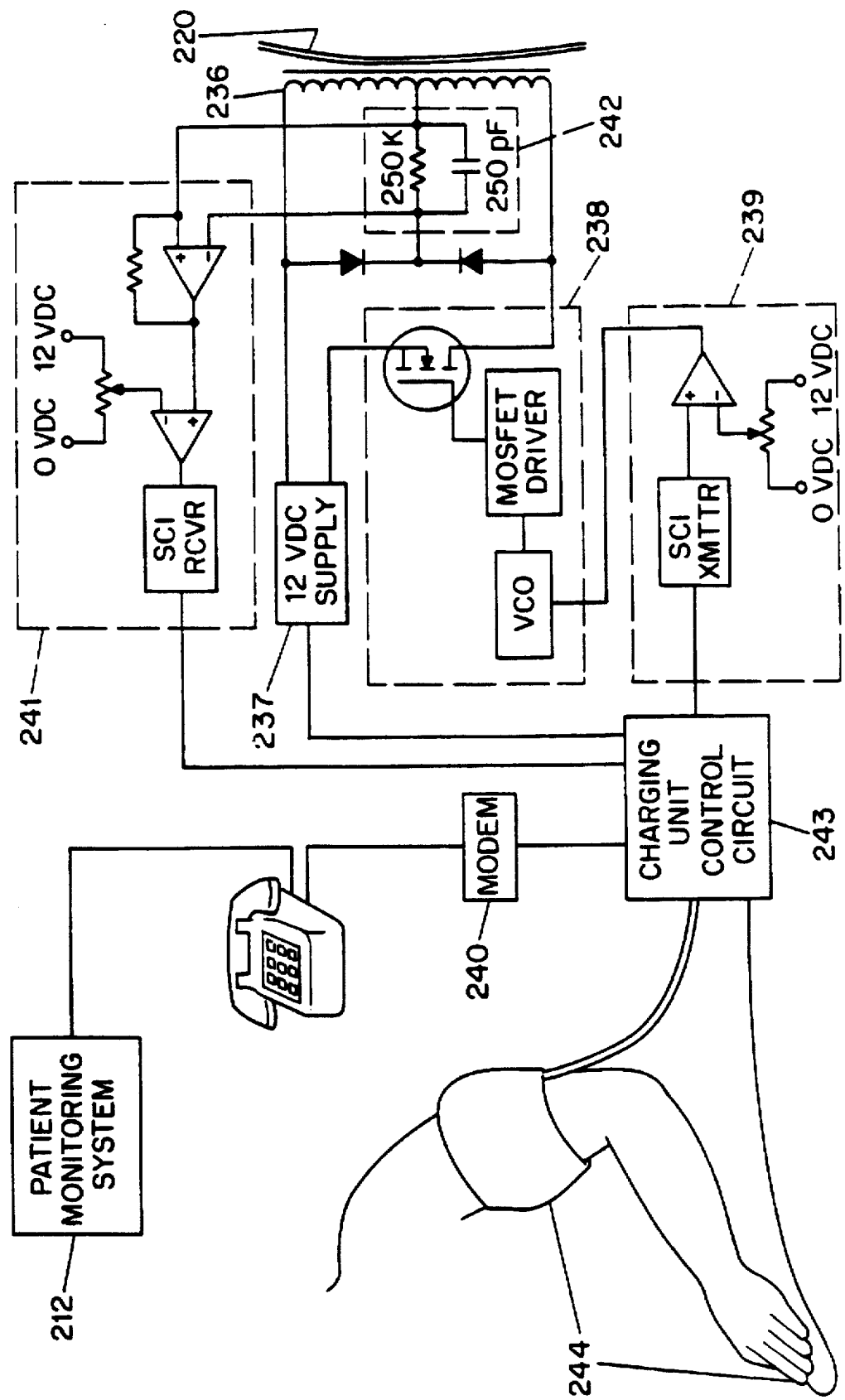
Figure 10:
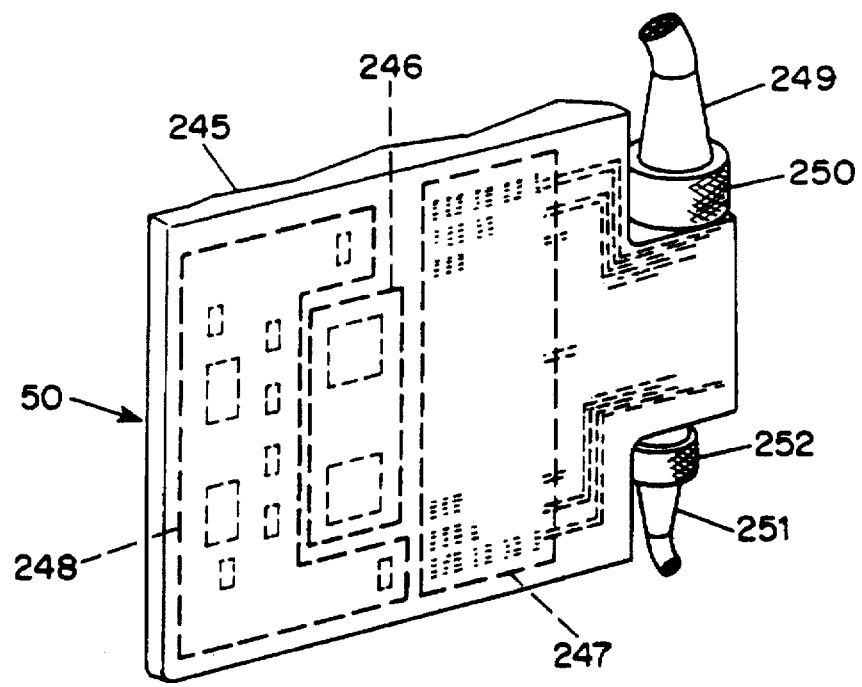
FIGS. 10(a) and 10(b) are perspective views showing the opposite sides of an implantable controller arrangement in accordance with the invention.
Figure 10:
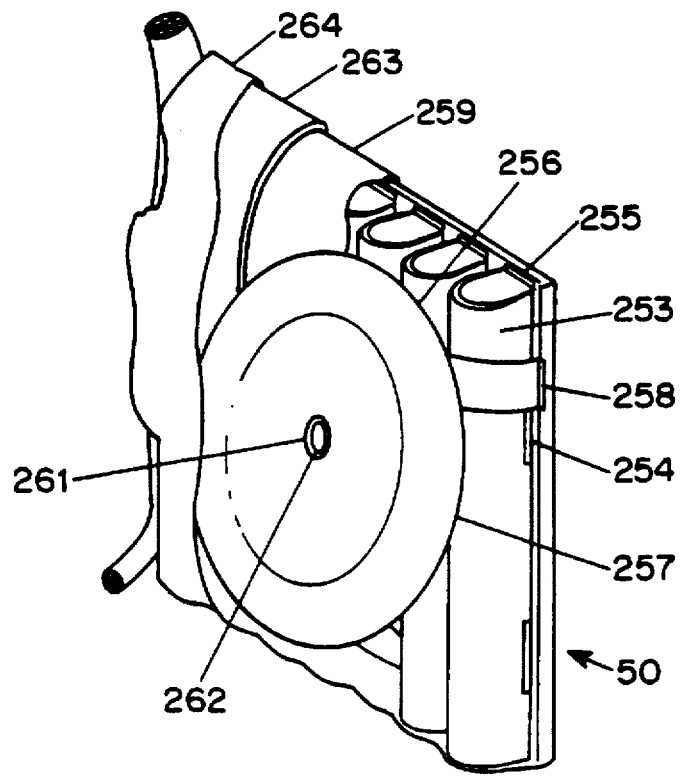
Figure 11:
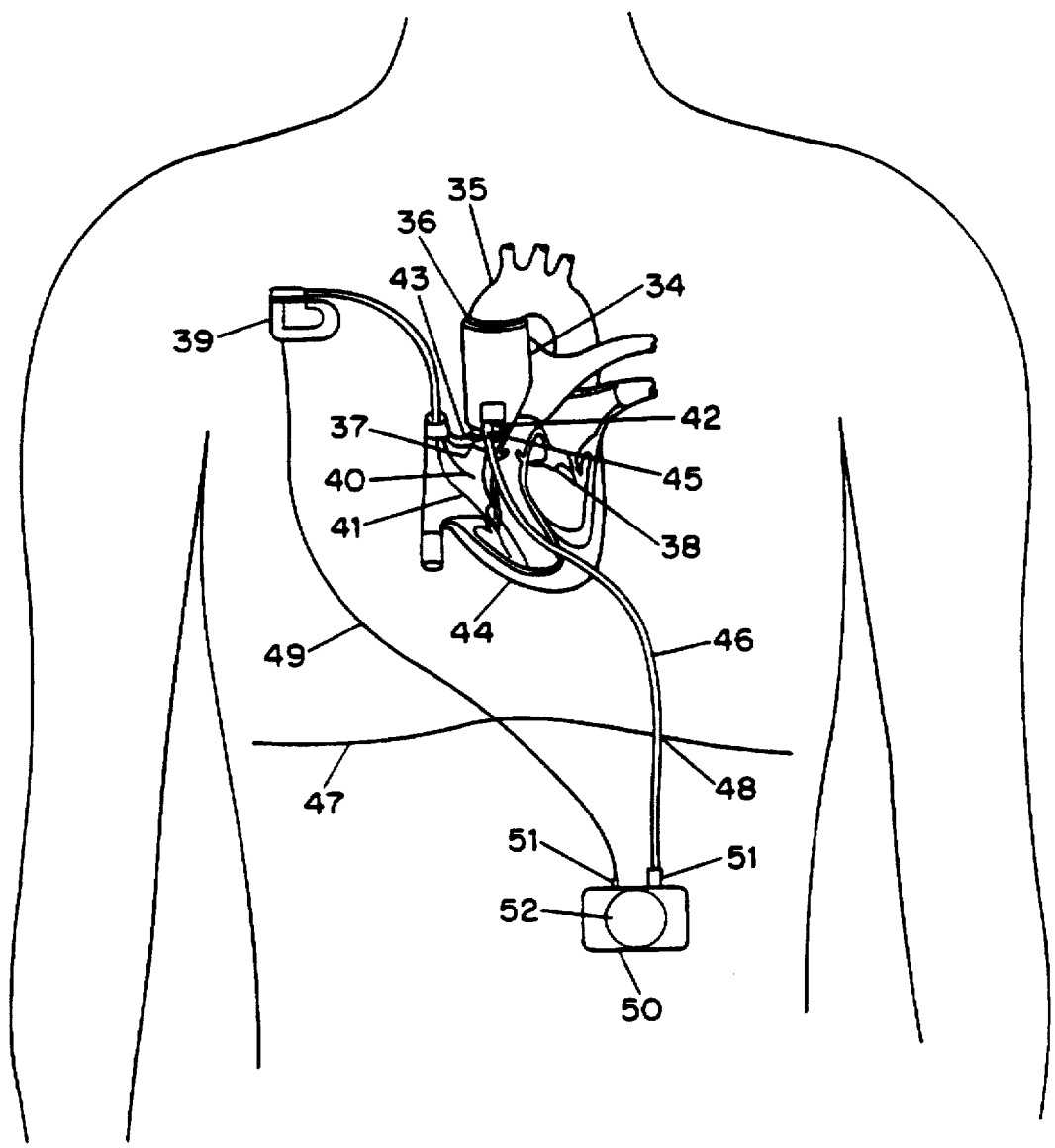
FIG. 11 is a schematic illustration showing the anatomical arrangement of a surgically implantable pump with a reciprocating piston-valve in accordance with the invention implanted as a left ventricular assist device.
Figure 12:
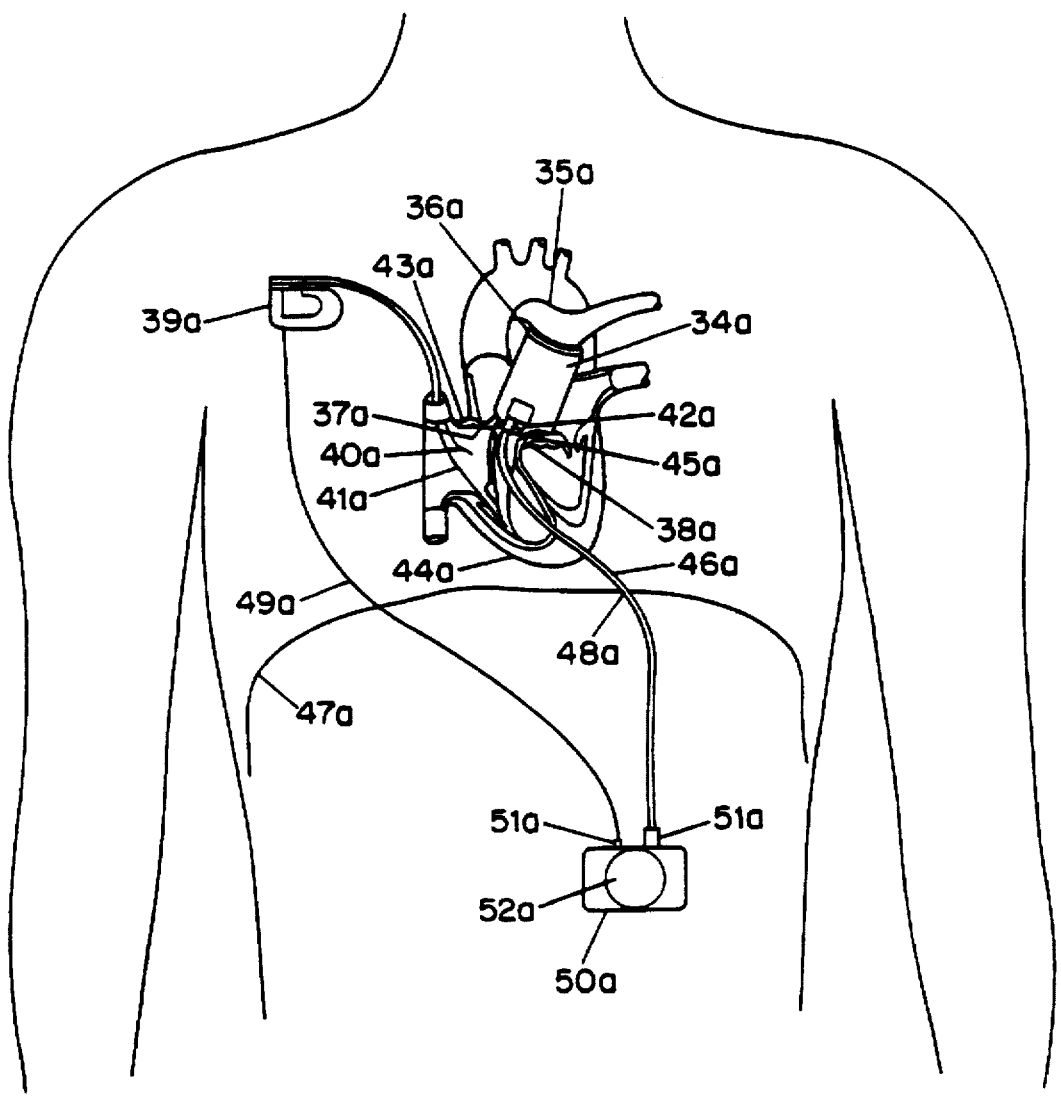
FIG. 12 is a schematic illustration showing the anatomical arrangement of a surgically implantable pump with a reciprocating piston-valve in accordance with the invention implanted as a simplex right ventricular assist device.
Figure 13:
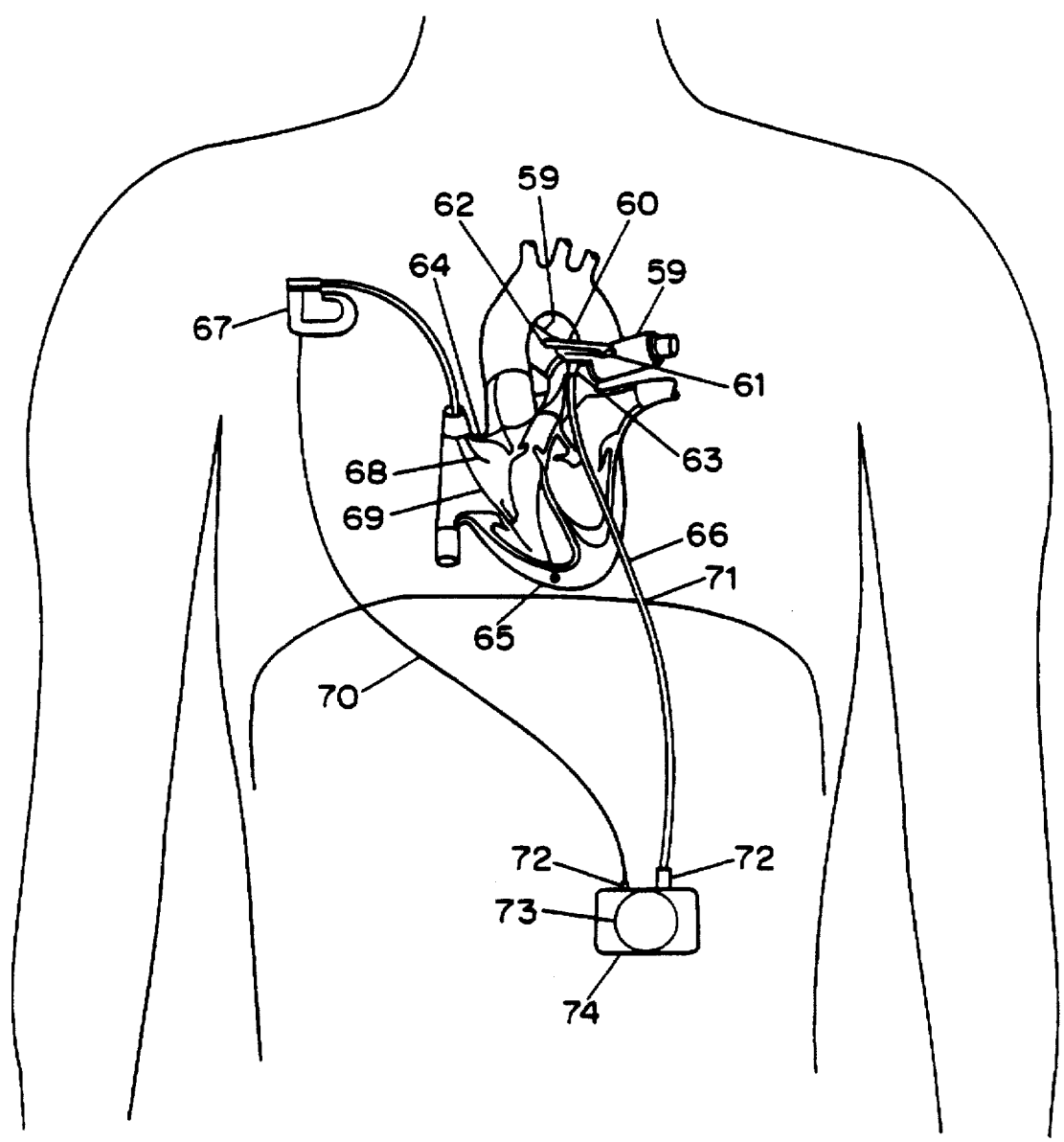
FIG. 13 is a schematic illustration showing the anatomical arrangement of a surgically implantable pump arrangement in accordance with the invention implanted as a duplex right ventricular assist device.
Figure 14:
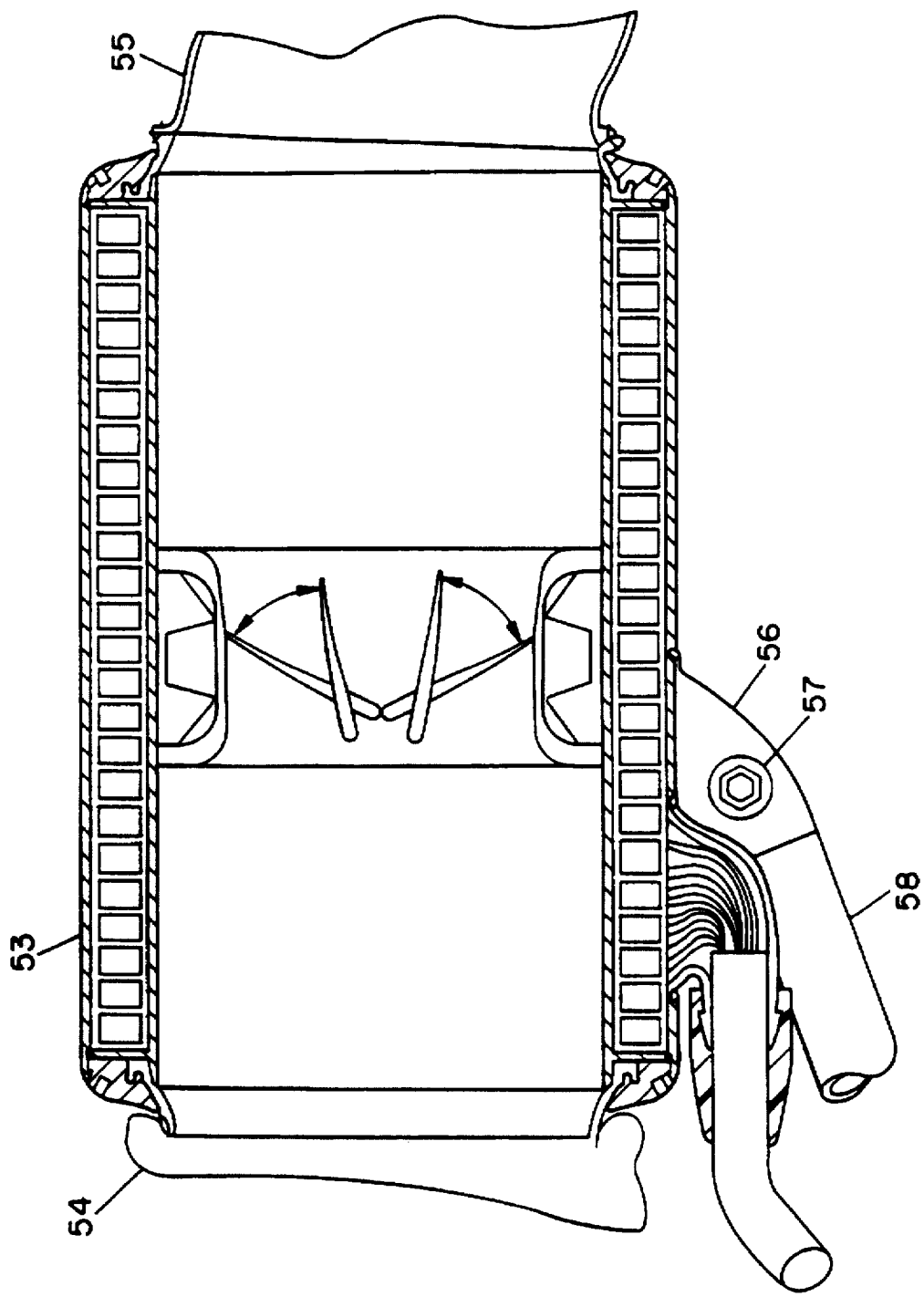
FIG. 14 is a longitudinal sectional view illustrating another embodiment of a surgically implantable pump arranged in accordance with the invention.
Figure 15:
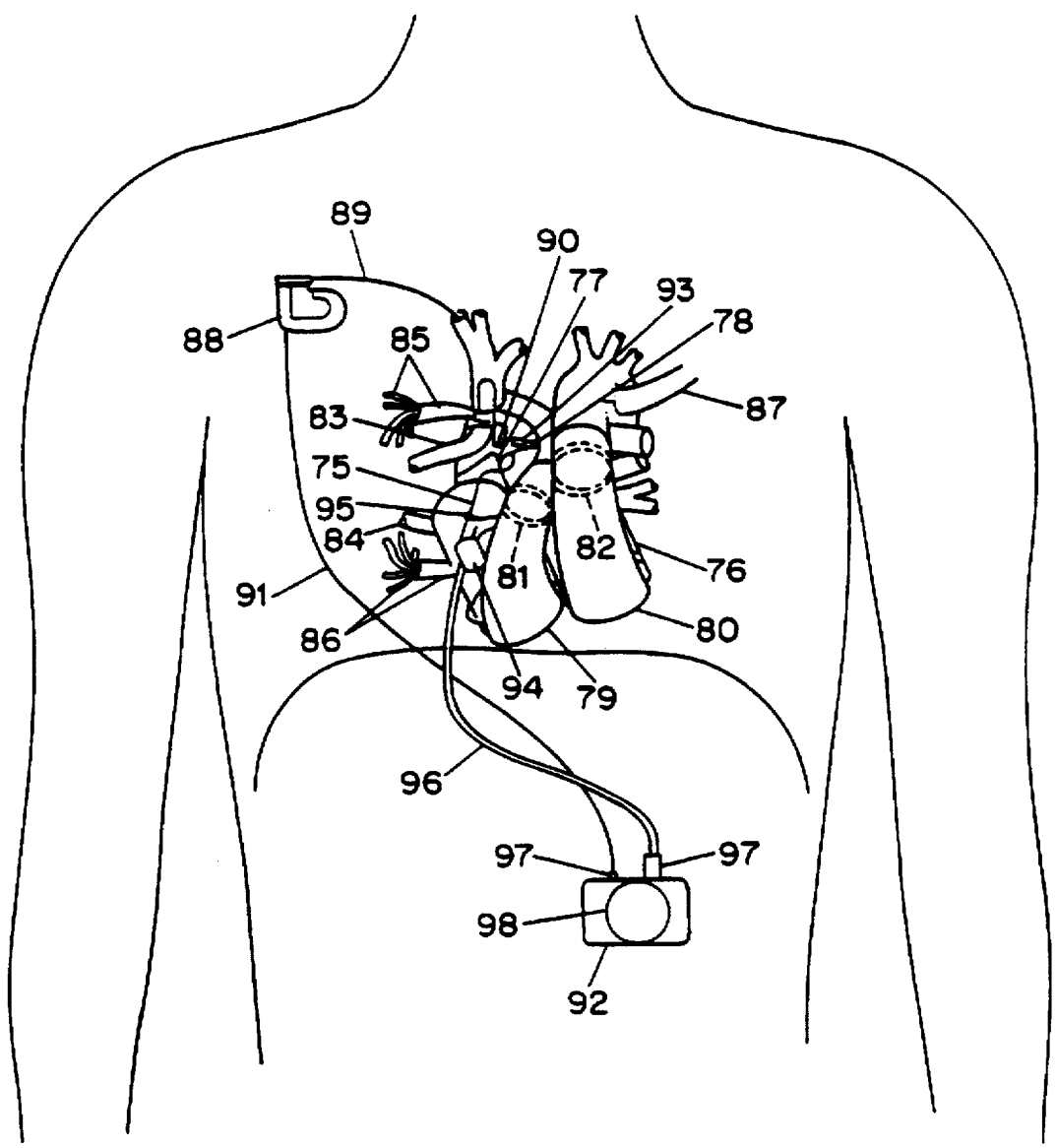
FIG. 15 is a schematic illustration showing the anatomical disposition of a surgically implantable pump arrangement in accordance with the invention in a duplex total artificial heart implantation.
Figure 16:
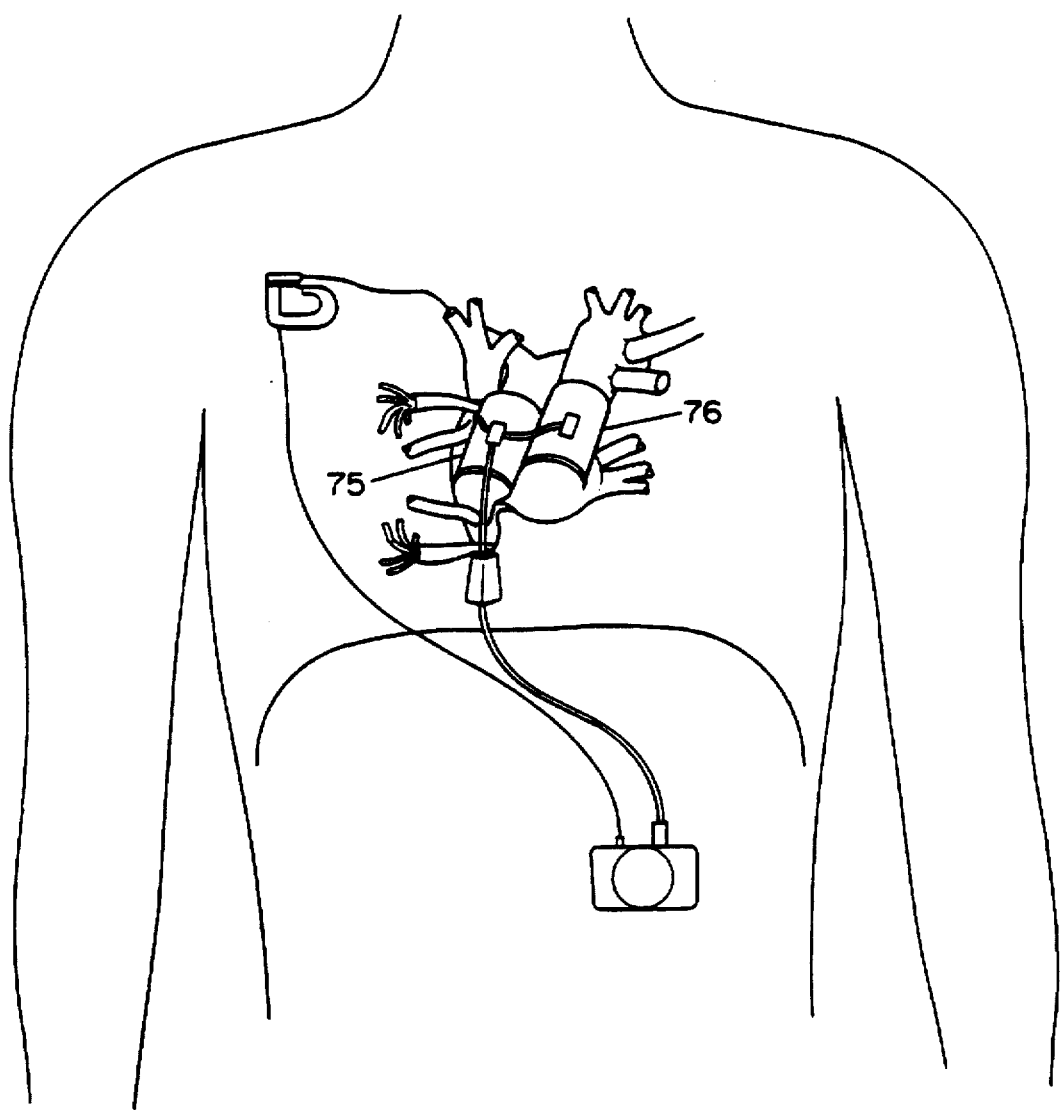
FIG. 16 is a representative alternate surgically implantable pump arrangement in accordance with the invention in a duplex total artificial heart implantation.

An alternate arrangement of the permanent magnets used in the pistons shown in FIGS. 1, 4 and 5 is shown in FIG. 6. In this arrangement, two annular permanent magnets 450, 451 have a radial magnetic pole orientation. A magnetically soft ferromagnetic material 452 such as iron-cobalt material couples the poles on the inner surfaces of the annular magnet to provide a low reluctance path for the flux passing through the outer surfaces of the permanent magnets.

Although the pump described herein may be used in implantable blood pumps, it is also useful as a blood pump which is not surgically implanted inside the body of a patient. In particular, pumps in accordance with the invention might be useful in cardiopulmonary bypass machines, which are used during cardiac surgery but which are not implanted in the patient's body, or in extracorporeal cardiac support devices. The pump module of the invention may also be used as a compact, efficient pump for conveying liquids other than blood.

Although the invention has been described herein with reference to specific embodiments, many modifications and variations therein will readily occur to those skilled in the art. Accordingly, all such variations and modifications are included within the intended scope of the invention.

We claim:

1. A connecting arrangement for connecting a medical device including a hollow cylinder to a vessel in a human body comprising a metal ring, and a two-part sewing ring attached at one end to the metal ring, the two-part sewing ring comprising an endothelial promoting outer covering and a compliant inner layer connected at one end to the metal ring and connectable at the other end to a vessel in the human body, an exposed portion of the metal ring opposite to the sewing ring being removably connectible to the hollow cylinder.

2. A connecting arrangement according to claim 1 including a medical device to be connected to the metal ring, and connecting means on the medical device and on the metal ring comprising a plurality of resiliently interengagable projections and spaced individual recesses arranged to be interlocked upon motion in an axial direction toward each other and to be disengaged by relative rotary motion and axial motion away from each other.

3. A connecting arrangement according to claim 2 wherein the medical device includes movable element and the metal ring prevents the movable element from traveling beyond the end of the medical device.

4. A connecting arrangement for connecting a medical device including a hollow cylinder to a vessel in a human body comprising a retaining ring and a removable sewing ring, the sewing ring comprising biocompatible surgical graft material and removably connected at one end to the retaining ring and connectable at the other end to a vessel in the human body, an exposed portion of the retaining ring opposite to the sewing ring being removably connectible to the hollow cylinder.

5. A connecting arrangement according to claim 4 including a medical device to be connected to the retaining ring, and connecting means on the medical device and on the retaining ring comprising a plurality of resiliently interengagable projections and spaced individual recesses arranged to be interlocked upon motion in an axial direction toward each other and to be disengaged by relative rotary motion and axial motion away from each other.

6. A connecting arrangement according to claim 5 wherein the medical device includes a movable element and the retaining ring prevents the movable element from traveling beyond the end of the medical device.

7. A method for connecting a medical device to a vessel in a human body comprising the steps of:

providing a retaining ring and a removable sewing ring, the sewing ring comprising biocompatible surgical graft material, removably connecting the sewing ring at one end to the retaining ring, providing a connecting means on the medical device and retaining ring having a plurality of resiliently interengagable projections and spaced individual recesses which interlock upon motion in an axial direction toward each other and disengage by relating rotary motion and axial motion away from each other, removably connecting an exposed end of the retaining ring to the medical device by interlocking the interengagable projections and spaced individual recesses, and connecting the other end of the sewing ring to a vessel in the human body.

8. A method according to claim 7 wherein the medical device includes a movable element and the retaining ring prevents the movable element from traveling beyond the end of the medical device.

\* \* \* \* \*